United States Patent
Swem et al.

(10) Patent No.: US 9,745,365 B2
(45) Date of Patent: Aug. 29, 2017

(54) ANTI-INFLUENZA B VIRUS HEMAGGLUTININ ANTIBODIES AND METHODS OF USE

(71) Applicant: Genentech, Inc., South San Francisco, CA (US)

(72) Inventors: Lee Swem, Montara, CA (US); Min Xu, Millbrae, CA (US); Mercedesz Balazs, Seattle, WA (US); Ning Chai, Dublin, CA (US); Nancy Chiang, San Francisco, CA (US); Henry Chiu, San Francisco, CA (US); Zhonghua Lin, San Francisco, CA (US); Gerald R. Nakamura, San Francisco, CA (US); Hyunjoo Park, San Leandro, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/669,317

(22) Filed: Mar. 26, 2015

(65) Prior Publication Data
US 2015/0274812 A1    Oct. 1, 2015

Related U.S. Application Data

(60) Provisional application No. 61/971,123, filed on Mar. 27, 2014.

(51) Int. Cl.
| | | |
|---|---|---|
| C07K 16/10 | (2006.01) | |
| A61K 31/215 | (2006.01) | |
| A61K 39/395 | (2006.01) | |
| A61K 45/06 | (2006.01) | |
| A61K 39/00 | (2006.01) | |

(52) U.S. Cl.
CPC ........ *C07K 16/1018* (2013.01); *A61K 31/215* (2013.01); *A61K 39/39583* (2013.01); *A61K 45/06* (2013.01); *A61K 2039/505* (2013.01); *C07K 2317/51* (2013.01); *C07K 2317/515* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 2009/0092620 A1 | 4/2009 | Moste |
| 2011/0319600 A1 | 12/2011 | Ikuta |
| 2011/0319660 A1 | 12/2011 | Coszach et al. |

FOREIGN PATENT DOCUMENTS

| | | |
|---|---|---|
| WO | 2010/073647 A1 | 7/2010 |
| WO | 2013/007770 A1 | 1/2013 |
| WO | 2013/114885 A1 | 8/2013 |
| WO | 2013/132007 A1 | 9/2013 |

OTHER PUBLICATIONS

Dreyfus et al., "Highly Conserved Protective Epitopes on Influenza B Viruses" Science 337:1343-1348 (2012).
International Search Report and Written Opinion for PCT/US2015/022758.
Kubota-Koketsu et al., "Broad neutralizing human monoclonal antibodies against influenza virus from vaccinated healthy donors" Biochemical and Biophysical Research Communications 387:180-185 (2009).
Nakagawa et al., "Rapid detection and identification of two lineages of influenza B strains with monoclonal antibodies" J Virol Methods 79:113-20 (Apr. 1999).
Nakamura et al., "An In Vivo Human-Plasmablast Enrichment Technique Allows Rapid Identification of Therapeutic Influenza A Antibodies"Cell Host & Microbe 14:93-103 (Jul. 2013).
Yasugi et al., "Human Monoclonal Antibodies Broadly Neutralizing against Influenza B Virus" PLOS Pathogens 9(2):e1003150 (Feb. 2013).

*Primary Examiner* — Nicole Kinsey White
(74) *Attorney, Agent, or Firm* — James E. Nesbitt

(57) ABSTRACT

The present invention provides anti-influenza B virus hemagglutinin antibodies, compositions comprising anti-influenza B virus hemagglutinin antibodies, and methods of using the same.

15 Claims, 22 Drawing Sheets

| mAb | CDR L1 | CDR L2 | CDR L3 | CDR H1 | CDR H2 | CDR H3 |
|---|---|---|---|---|---|---|
| 34B5A | TGTSDIGSYNYVS (SEQ ID NO: 55) | EVSQRPS (SEQ ID NO: 57) | ASYAGNNIYV (SEQ ID NO: 59) | GYYIH (SEQ ID NO: 61) | RIDPNGSGTTYAQKFQG (SEQ ID NO: 64) | WDWNFDLYLGWFDP (SEQ ID NO: 75) |
| 34B5B | TGTSDIGSYNYVS (SEQ ID NO: 55) | EVSQRPS (SEQ ID NO: 57) | ASYAGNNIYV (SEQ ID NO: 59) | GYYIH (SEQ ID NO: 61) | RIDPNGAGTTYAQKFQG (SEQ ID NO: 65) | WDWNFDLYLGWFDP (SEQ ID NO: 75) |
| 34B5C | TGTSDIGSYNYVS (SEQ ID NO: 55) | EVSQRPS (SEQ ID NO: 57) | ASYAGNNIYV (SEQ ID NO: 59) | GYYIH (SEQ ID NO: 61) | RIDPNGAGTTYAQKFQG (SEQ ID NO: 65) | WDWNFDLYLGWFDP (SEQ ID NO: 75) |
| 33F8 | TGTSDIGSYNYVS (SEQ ID NO: 55) | EVSQRPS (SEQ ID NO: 57) | ASYAGNNIYV (SEQ ID NO: 59) | AHHMH (SEQ ID NO: 62) | WIDPNNDGTIYAQKFQG (SEQ ID NO: 66) | WAWNFDFFLGWFDP (SEQ ID NO: 76) |
| 46B8A | RSSQSLLRSNGYNYLD (SEQ ID NO: 56) | LGSNRAS (SEQ ID NO: 58) | MQALQTPYT (SEQ ID NO: 60) | SQWIG (SEQ ID NO: 63) | MMYPGDSDTIYSPSFQG (SEQ ID NO: 67) | GPGYSGYHYGWFDT (SEQ ID NO: 77) |
| 46B8B | RSSQSLLRSNGYNYLD (SEQ ID NO: 56) | LGSNRAS (SEQ ID NO: 58) | MQALQTPYT (SEQ ID NO: 60) | SQWIG (SEQ ID NO: 63) | MMYPGDADAIYSPSFQG (SEQ ID NO: 68) | GPGYSGYHYGWFDT (SEQ ID NO: 77) |
| 46B8C | RSSQSLLRSNGYNYLD (SEQ ID NO: 56) | LGSNRAS (SEQ ID NO: 58) | MQALQTPYT (SEQ ID NO: 60) | SQWIG (SEQ ID NO: 63) | MMYPGESETIYSPSFQG (SEQ ID NO: 69) | GPGYSGYHYGWFDT (SEQ ID NO: 77) |
| 46B8D | RSSQSLLRSNGYNYLD (SEQ ID NO: 56) | LGSNRAS (SEQ ID NO: 58) | MQALQTPYT (SEQ ID NO: 60) | SQWIG (SEQ ID NO: 63) | MMYPGDADTIYSPSFQG (SEQ ID NO: 70) | GPGYSGYHYGWFDT (SEQ ID NO: 77) |
| 46B8E | RSSQSLLRSNGYNYLD (SEQ ID NO: 56) | LGSNRAS (SEQ ID NO: 58) | MQALQTPYT (SEQ ID NO: 60) | SQWIG (SEQ ID NO: 63) | MMYPGSSDTIYSPSFQG (SEQ ID NO: 71) | GPGYSGYHYGWFDT (SEQ ID NO: 77) |
| 46B8F | RSSQSLLRSNGYNYLD (SEQ ID NO: 56) | LGSNRAS (SEQ ID NO: 58) | MQALQTPYT (SEQ ID NO: 60) | SQWIG (SEQ ID NO: 63) | MMYPGDSDAIYSPSFQG (SEQ ID NO: 72) | GPGYSGYHYGWFDT (SEQ ID NO: 77) |
| 46B8G | RSSQSLLRSNGYNYLD (SEQ ID NO: 56) | LGSNRAS (SEQ ID NO: 58) | MQALQTPYT (SEQ ID NO: 60) | SQWIG (SEQ ID NO: 63) | MMYPGDTDTIYSPSFQG (SEQ ID NO: 73) | GPGYSGYHYGWFDT (SEQ ID NO: 77) |
| 46B8H | RSSQSLLRSNGYNYLD (SEQ ID NO: 56) | LGSNRAS (SEQ ID NO: 58) | MQALQTPYT (SEQ ID NO: 60) | SQWIG (SEQ ID NO: 63) | MMYPGESDTIYSPSFQG (SEQ ID NO: 74) | GPGYSGYHYGWFDT (SEQ ID NO: 77) |

FIG. 13 mAb 34B5A

Light Chain Variable Region
QSVLTQPPSASGSRGQSITISCTGSTSDIGSYNYVSWYQQHPGTAPKVILYEVSQRPSGVPDRFSGSKSGNTAFLTVSGLQTDDEADYY
CASYAGNNIYVFGSGTKVT (SEQ ID NO: 78)

Heavy Chain Variable Region
QVQLVQSGAEVKKPGASVKVSCKASGYIFTGYYIHWVRQAPGQGLEWMGRIDPNGSGTTYAQKFQGRVTLTMDTSITTAYMELSRLRFD
DTAIYYCARWDWNFDLYLGWFDPWGQGTPVTVAS (SEQ ID NO: 79)

Light Chain
QSVLTQPPSASGSRGQSITISCTGSTSDIGSYNYVSWYQQHPGTAPKVILYEVSQRPSGVPDRFSGSKSGNTAFLTVSGLQTDDEADYY
CASYAGNNIYVFGSGTKVTVLGQPKANPTVTLFPPSSEELQANKATLVCLISDFYPGAVTVAWKADSSPVKAGVETTTPSKQSNNKYAA
SSYLSLTPEQWKSHKSYSCQVTHEGSTVEKTVAPTECS (SEQ ID NO: 80)

Heavy Chain
QVQLVQSGAEVKKPGASVKVSCKASGYIFTGYYIHWVRQAPGQGLEWMGRIDPNGSGTTYAQKFQGRVTLTMDTSITTAYMELSRLRFD
DTAIYYCARWDWNFDLYLGWFDPWGQGTPVTVASASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 81)

FIG. 14 mAb 34B5B

Light Chain Variable Region

SVLTQPPSASGSSRGQSITISCTGSTSDIGSYNYVSWYQQHPGTAPKVILYEVSQRPSGVPDRFSGSKSGNTAFLTVSGLQAEDEADYYC
ASYAGNNIYVFGSGTKVT (SEQ ID NO: 82)

Heavy Chain Variable Region

EVQLVQSGAEVKKPGASVKVSCKASGYIFTGYYIHWVRQAPGQGLEWMGRIDPNGAGTTYAQKFQGRVTLTMDTSITTAYMELSRLRFD
DTAIYYCARWDWNFDLYLGWFDPWGQGTPVTVAS (SEQ ID NO: 83)

Light Chain

SVLTQPPSASGSSRGQSITISCTGSTSDIGSYNYVSWYQQHPGTAPKVILYEVSQRPSGVPDRFSGSKSGNTAFLTVSGLQAEDEADYYC
ASYAGNNIYVFGSGTKVTVLGQPKANPTVTLFPPSSEELQANKATLVCLISDFYPGAVTVAWKADSSPVKAGVETTTPSKQSNNKYAAS
SYLSLTPEQWKSHKSYSCQVTHEGSTVEKTVAPTECS (SEQ ID NO: 84)

Heavy Chain

EVQLVQSGAEVKKPGASVKVSCKASGYIFTGYYIHWVRQAPGQGLEWMGRIDPNGAGTTYAQKFQGRVTLTMDTSITTAYMELSRLRFD
DTAIYYCARWDWNFDLYLGWFDPWGQGTPVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 85)

FIG. 15 mAb 34B5C

Light Chain Variable Region
SALTQPPSASGSRGQSITISCTGSTSDIGSYNYVSWYQQHPGTAPKVILYEVSQRPSGVPDRFSGSKSGNTAFLTVSGLQAEDEADYYC
ASYAGNNIYVFGSGTKVT (SEQ ID NO: 86)

Heavy Chain Variable Region
EVQLVQSGAEVKKPGASVKVSCKASGYIFTGYYIHWVRQAPGQGLEWMGRIDPNGAGTTYAQKFQGRVTLTMDTSITTAYMELSRLRFD
DTAIYYCARWDNNFDLYLGWFDPWGQGTPVTVAS (SEQ ID NO: 83)

Light Chain
SALTQPPSASGSRGQSITISCTGSTSDIGSYNYVSWYQQHPGTAPKVILYEVSQRPSGVPDRFSGSKSGNTAFLTVSGLQAEDEADYYC
ASYAGNNIYVFGSGTKVTVLGQPKANPTVTLFPPSSEELQANKATLVCLISDFYPGAVTVAWKADSSPVKAGVETTTPSKQSNNKYAAS
SYLSLTPEQWKSHKSYSCQVTHEGSTVEKTVAPTECS (SEQ ID NO: 87)

Heavy Chain
EVQLVQSGAEVKKPGASVKVSCKASGYIFTGYYIHWVRQAPGQGLEWMGRIDPNGAGTTYAQKFQGRVTLTMDTSITTAYMELSRLRFD
DTAIYYCARWDNNFDLYLGWFDPWGQGTPVTVASASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 88)

FIG. 16 mAb 33F8

Light Chain Variable Region
QSVLTQPPSASGSRGQSITISCTGSTSDIGSYNYVSWYQQHPGTAPKVILYEVSQRPSGVPDRFSGSKSGNTAFLTVSGLQTDDEADYY
CASYAGNNIYVFGSGTKVT (SEQ ID NO: 78)

Heavy Chain Variable Region
QVQLVQSGAEVKKPGASVKVSCKASGYTFNAHHMHWVRQAPGQGLGWMGWIDPNNDGTIYAQKFQGRVTLTMDTSIHTAYMELSGLRYD
DTAIYYCVRWAWNFDFFLGWFDPWGQGTLVTVAS (SEQ ID NO: 89)

Light Chain
QSVLTQPPSASGSRGQSITISCTGSTSDIGSYNYVSWYQQHPGTAPKVILYEVSQRPSGVPDRFSGSKSGNTAFLTVSGLQTDDEADYY
CASYAGNNIYVFGSGTKVTVLGQPKANPTVTLFPPSSEELQANKATLVCLISDFYPGAVTVAWKADSSPVKAGVETTTPSKQSNNKYAA
SSYLSLTPEQWKSHKSYSCQVTHEGSTVEKTVAPTECS (SEQ ID NO: 80)

Heavy Chain
QVQLVQSGAEVKKPGASVKVSCKASGYTFNAHHMHWVRQAPGQGLGWMGWIDPNNDGTIYAQKFQGRVTLTMDTSIHTAYMELSGLRYD
DTAIYYCVRWAWNFDFFLGWFDPWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 90)

FIG. 17 mAb 46B8A

Light Chain Variable Region
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIK (SEQ ID NO: 91)

Heavy Chain Variable Region
EVQLVQSGAEVKKPGESLKISCKVSGYSFTSQWIGWVRQMPGKGLEWIGMMYPGDSDTIYSPSFQGQVTISADNSISTAYLQWSSLKAS
DTAIYYCASGPGYSGYHYGWFDTWGQGTLVTVSS (SEQ ID NO: 92)

Light Chain
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIKRTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 93)

Heavy Chain
EVQLVQSGAEVKKPGESLKISCKVSGYSFTSQWIGWVRQMPGKGLEWIGMMYPGDSDTIYSPSFQGQVTISADNSISTAYLQWSSLKAS
DTAIYYCASGPGYSGYHYGWFDTWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 94)

FIG. 18 mAb 46B8B

Light Chain Variable Region
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIK (SEQ ID NO: 91)

Heavy Chain Variable Region
EVQLVQSGAEVKKPGESLKISCKVSGYSFTSQWIGWVRQMPGKGLEWIGMMYPGDADAIYSPSFQGQVTISADNSISTAYLQWSSLKAS
DTAIYYCASGPGYSGYHYGWFDTWGQGTLVTVSS (SEQ ID NO: 95)

Light Chain
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIKRTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 93)

Heavy Chain
EVQLVQSGAEVKKPGESLKISCKVSGYSFTSQWIGWVRQMPGKGLEWIGMMYPGDADAIYSPSFQGQVTISADNSISTAYLQWSSLKAS
DTAIYYCASGPGYSGYHYGWFDTWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 96)

FIG. 19 mAb 46B8C

Light Chain Variable Region
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIK (SEQ ID NO: 91)

Heavy Chain Variable Region
EVQLVQSGAEVKKPGESLKISCKVSGYSFTSQWIGWVRQMPGKGLEWIGMMYPGESETIYSPSFQGQVTISADNSISTAYLQWSSLKAS
DTAIYYCASGPGYSGYHYGWFDTWGQGTLVTVSS (SEQ ID NO: 97)

Light Chain
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIKRTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 93)

Heavy Chain
EVQLVQSGAEVKKPGESLKISCKVSGYSFTSQWIGWVRQMPGKGLEWIGMMYPGESETIYSPSFQGQVTISADNSISTAYLQWSSLKAS
DTAIYYCASGPGYSGYHYGWFDTWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 98)

*FIG. 20* mAb 46B8D

Light Chain Variable Region
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIK (SEQ ID NO: 91)

Heavy Chain Variable Region
EVQLVQSGAEVKKPGESLKISCKVSGYSFTSQWIGWVRQMPGKGLEWIGMMYPGDADTIYSPSFQGQVTISADNSISTAYLQWSSLKAS
DTAIYYCASGPGYSGYHYGWFDTWGQGTLVTVSS (SEQ ID NO: 99)

Light Chain
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIKRTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 93)

Heavy Chain
EVQLVQSGAEVKKPGESLKISCKVSGYSFTSQWIGWVRQMPGKGLEWIGMMYPGDADTIYSPSFQGQVTISADNSISTAYLQWSSLKAS
DTAIYYCASGPGYSGYHYGWFDTWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 100)

FIG. 21 mAb 46B8E

Light Chain Variable Region
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIK (SEQ ID NO: 91)

Heavy Chain Variable Region
EVQLVQSGAEVKKPGESLKISCKVSGYSFTSQWIGWVRQMPGKGLEWIGMMYPGSSDTIYSPSFQGQVTISADNSISTAYLQWSSLKAS
DTAIYYCASGPGYSGYHYGWFDTWGQGTLVTVSS (SEQ ID NO: 101)

Light Chain
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIKRTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 93)

Heavy Chain
EVQLVQSGAEVKKPGESLKISCKVSGYSFTSQWIGWVRQMPGKGLEWIGMMYPGSSDTIYSPSFQGQVTISADNSISTAYLQWSSLKAS
DTAIYYCASGPGYSGYHYGWFDTWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 102)

FIG. 22 mAb 46B8F

Light Chain Variable Region
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIK (SEQ ID NO: 91)

Heavy Chain Variable Region
EVQLVQSGAEVKKPGESLKISCKVSGYSFTSQWIGWVRQMPGKGLEWIGMMYPGDSDAIYSPSFQGQVTISADNSISTAYLQWSSLKAS
DTAIYYCASGPGYSGYHYGWFDTWGQGTLVTVSS (SEQ ID NO: 103)

Light Chain
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIKRTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 93)

Heavy Chain
EVQLVQSGAEVKKPGESLKISCKVSGYSFTSQWIGWVRQMPGKGLEWIGMMYPGDSDAIYSPSFQGQVTISADNSISTAYLQWSSLKAS
DTAIYYCASGPGYSGYHYGWFDTWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 104)

FIG. 23 mAb 46B8G

Light Chain Variable Region
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIK (SEQ ID NO: 91)

Heavy Chain Variable Region
EVQLVQSGAEVKKPGESLKISCKVSGYSFTSQWIGWVRQMPGKGLEWIGMMYPGDTDTIYSPSFQGQVTISADNSISTAYLQWSSLKAS
DTAIYYCASGPGYSGYHYGWFDTWGQGTLVTVSS (SEQ ID NO: 105)

Light Chain
DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIKRTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 93)

Heavy Chain
EVQLVQSGAEVKKPGESLKISCKVSGYSFTSQWIGWVRQMPGKGLEWIGMMYPGDTDTIYSPSFQGQVTISADNSISTAYLQWSSLKAS
DTAIYYCASGPGYSGYHYGWFDTWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 106)

*FIG. 24* mAb 46B8H

Light Chain Variable Region

DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIK (SEQ ID NO: 91)

Heavy Chain Variable Region

EVQLVQSGAEVKKPGESLKISCKVSGYSFTSQWIGWVRQMPGKGLEWIGMMYPGESDTIYSPSFQGQVTISADNSISTAYLQWSSLKAS
DTAIYYCASGPGYSGVHYGWFDTWGQGTLVTVSS (SEQ ID NO: 107)

Light Chain

DIVMTQSPLSLPVTPGEPASISCRSSQSLLRSNGYNYLDWYLQKPGQSPQLLIYLGSNRASGVPDRFSGSGSGTDFTLKISRVEAEDVG
VYYCMQALQTPYTFGQGTKLEIKRTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 93)

Heavy Chain

EVQLVQSGAEVKKPGESLKISCKVSGYSFTSQWIGWVRQMPGKGLEWIGMMYPGESDTIYSPSFQGQVTISADNSISTAYLQWSSLKAS
DTAIYYCASGPGYSGVHYGWFDTWGQGTLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK (SEQ ID NO: 108)

ANTI-INFLUENZA B VIRUS HEMAGGLUTININ ANTIBODIES AND METHODS OF USE

RELATED APPLICATIONS

This application claims the benefit of U.S. Provisional Application No. 61/971,123, filed on 27 Mar. 2014, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Mar. 18, 2015, is named P5794R1_US_SL.txt and is 94,387 bytes in size.

FIELD OF THE INVENTION

The present invention provides anti-influenza B virus hemagglutinin antibodies, compositions comprising anti-influenza B virus hemagglutinin antibodies, and methods of using the same.

BACKGROUND

Influenza virus infection causes between three and five million cases of severe illness and between 250,000 and 500,000 deaths every year around the world. In the United States alone, 5% to 20% of the population becomes infected with influenza virus each year, with the majority of these infections caused by influenza A virus. (See, e.g., Dushoff et al., (2006) Am J Epidemiology 163:181-187; Thompson et al., (2004) JAMA 292:1333-1340; Thompson et al., (2003) JAMA 289:179-186.) Influenza B virus infections, however, account for approximately 10,000-100,000 hospitalized influenza cases per year in the United States alone, displaying a high year-to-year variability (1%-40% of all hospitalized influenza virus cases are influenza B virus infections, with a mean of 17%). (See Zhou et al (2012) Clin Inf Dis 54:1427-1436.) The burden associated with influenza virus infection on health care costs and lost productivity is extensive. Hospitalization and deaths mainly occur in high-risk groups, such as the elderly, children, and chronically ill.

Neuraminidase inhibitors are approved for outpatient treatment and prophylaxis for influenza A and B virus infection. TAMIFLU® oseltamivir phosphate is a widely used prophylactic and early therapeutic treatment option for influenza A and B virus infection. (See, e.g., Kandel and Hartshorn (2001) BioDrugs: Clinical Immunotherapy, Biopharmaceuticals and Gene Therapy 15:303-323; Nicholson et al., (2000) Lancet 355:1845-1850; Treanor et al., (2000) JAMA 283:1016-1024; and Welliver et al., (2001) JAMA 285:748-754.) However, oseltamivir treatment must begin within 48 hours of symptom onset to provide a significant clinical benefit. (See, e.g., Aoki et al (2003) J Antimicrobial Chemotherapy 51:123-129.) This liability compromises oseltamivir's ability to treat severely ill patients, who are typically beyond the optimal 48-hour treatment window at the time of seeking treatment. Additionally, oseltamivir is less effective at treating influenza B virus infection compared to treating influenza A virus infection, perhaps due in part to its 10-fold higher IC50 value for influenza B neuraminidase compared to that for influenza A neuraminidase. Therefore, significant focus has recently been placed on identifying influenza B virus therapeutics to treat hospitalized influenza B virus infected patients.

During 1988-1989, two highly distinct antigenic variants of influenza B virus emerged from ancestral influenza B virus lineages. These viruses were antigenically related to either influenza B virus B/Victoria/2/87 or B/Yamagata/16/88. (See, e.g., Rota et al. (1990) Virology 175:59-68.) It is therefore desirable to develop a therapy for influenza B virus infection that is effective against ancestral, Victoria, and Yamagata lineages of influenza B virus.

Recent reports have described monoclonal antibodies (mAb) that bind hemagglutinin and neutralize influenza B virus. (See Kubota-Koketsu et al. (2009) Biochem Biophys Res Comm 387:180-185; Yasugi et al. (2013) PLOS Pathogens 9:e1003150, 1-12; Dreyfus et al. (2012) Science Express 337:1343-1348; International application publication numbers WO 2013/007770, WO 2013/132007, WO 2013/114885, WO 2010/073647, and U.S. application publication numbers US 2009/0092620, US 2011/0319600, and US 2011/0319660.)

Despite these reports, a need still exists in the art for novel influenza B virus therapies effective against a broad range of influenza B virus strains, including influenza B virus therapies effective at treating or preventing influenza B virus infection of ancestral, Yamagata, and Victoria lineages. The present invention meets this need and provides other benefits for the treatment and prevention of influenza B virus infection.

SUMMARY OF THE INVENTION

The present invention provides anti-influenza B virus hemagglutinin antibodies (i.e., anti-hemagglutinin antibodies, anti-influenza B virus antibodies), compositions comprising anti-influenza B virus hemagglutinin antibodies, and methods of using the same.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
 (a) HVR-H1 comprises the amino acid sequence of SEQ ID NO:61;
 (b) HVR-H2 comprises an amino acid sequence selected from the group consisting of SEQ ID NOs:64 and 65;
 (c) HVR-H3 comprises the amino acid sequence of SEQ ID NO:75;
 (d) HVR-L1 comprises the amino acid sequence of SEQ ID NO:55;
 (e) HVR-L2 comprises the amino acid sequence of SEQ ID NO:57; and
 (f) HVR-L3 comprises the amino acid sequence of SEQ ID NO:59.

In some embodiments, the invention provides an isolated anti-hemagglutinin antibody comprising: at least one, two, three, four, five and/or six hypervariable region (HVR) sequences, wherein:
 (a) HVR-H1 comprises the amino acid sequence of SEQ ID NO:61;
 (b) HVR-H2 comprises an amino acid sequence selected from the group consisting of SEQ ID NOs:64 and 65;
 (c) HVR-H3 comprises the amino acid sequence of SEQ ID NO:75;
 (d) HVR-L1 comprises the amino acid sequence of SEQ ID NOs:55;
 (e) HVR-L2 comprises the amino acid sequence of SEQ ID NO:57; and (f) HVR-L3 comprises the amino acid sequence of SEQ ID NO:59.

In some embodiments, the invention provides an isolated anti-hemagglutinin antibody comprising three light chain hypervariable regions (HVR-L1, HVR-L2, and LVR-L3), wherein:
(a) HVR-L1 comprises the amino acid sequence of SEQ ID NO:55;
(b) HVR-L2 comprises the amino acid sequence of SEQ ID NO:57; and
(c) HVR-L3 comprises the amino acid sequence of SEQ ID NO:59.

In some embodiments, the invention provides an isolated anti-hemagglutinin antibody comprising three heavy chain hypervariable regions (HVR-H1, HVR-H2, and HVR-H3), wherein:
(a) HVR-H1 comprises the amino acid sequence of SEQ ID NO:61;
(b) HVR-H2 comprises an amino acid sequence selected from the group consisting of SEQ ID NOs:64 and 65; and
(c) HVR-H3 comprises the amino acid sequence of SEQ ID NO:75.

In some embodiments, the invention provides an isolated anti-hemagglutinin antibody comprising: at least one, two, and/or three light chain hypervariable region (HVR) sequences, wherein:
(a) HVR-L1 comprises the amino acid sequence of SEQ ID NO:55;
(b) HVR-L2 comprises the amino acid sequence of SEQ ID NO:57; and
(c) HVR-L3 comprises the amino acid sequence of SEQ ID NO:59.

In some embodiments, the invention provides an isolated anti-hemagglutinin antibody comprising: at least one, two, and/or three heavy chain hypervariable region (HVR) sequences, wherein:
(a) HVR-H1 comprises the amino acid sequence of SEQ ID NO:61;
(b) HVR-H2 comprises an amino acid sequence selected from the group consisting of SEQ ID NOs:64 and 65; and
(c) HVR-H3 comprises the amino acid sequence of SEQ ID NO:75.

In some embodiments, an isolated anti-hemagglutinin antibody of the present invention comprises a heavy chain variable region and a light chain variable region, wherein the heavy chain variable region comprises an amino acid sequence selected from the group consisting of SEQ ID NOs:79 and 83, and the light chain variable region comprises an amino acid sequence selected from the group consisting of SEQ ID NOs:78, 82, and 86.

In some embodiments, an isolated anti-hemagglutinin antibody of the present invention comprises a light chain variable region comprising an amino acid sequence selected from the group consisting of SEQ ID NOs:78, 82, and 86.

In some embodiments, an isolated anti-hemagglutinin antibody of the present invention comprises a heavy chain variable region comprises an amino acid sequence selected from the group consisting of SEQ ID NOs:79 and 83.

In some embodiments, an isolated anti-hemagglutinin antibody of the present invention comprises a heavy chain and a light chain, wherein the heavy chain comprises an amino acid sequence selected from the group consisting of SEQ ID NOs:81, 85, and 88, and the light chain comprises an amino acid sequence selected from the group consisting of SEQ ID NOs:80, 84, and 87.

In some embodiments, an isolated anti-hemagglutinin antibody of the present invention comprises a light chain comprising an amino acid sequence selected from the group consisting of SEQ ID NOs:80, 84, and 87.

In some embodiments, an isolated anti-hemagglutinin antibody of the present invention comprises a heavy chain comprising an amino acid sequence selected from the group consisting of SEQ ID NOs:81, 85, and 88.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:62;
(b) HVR-H2 comprises the amino acid sequence of SEQ ID NO:66;
(c) HVR-H3 comprises the amino acid sequence of SEQ ID NO:76;
(d) HVR-L1 comprises the amino acid sequence of SEQ ID NO:55;
(e) HVR-L2 comprises the amino acid sequence of SEQ ID NO:57; and
(f) HVR-L3 comprises the amino acid sequence of SEQ ID NO:59.

In some embodiments, the invention provides an isolated anti-hemagglutinin antibody comprising: at least one, two, three, four, five and/or six hypervariable region (HVR) sequences, wherein:
(a) HVR-H1 comprises the amino acid sequence of SEQ ID NO:62;
(b) HVR-H2 comprises the amino acid sequence of SEQ ID NO:66;
(c) HVR-H3 comprises the amino acid sequence of SEQ ID NO:76;
(d) HVR-L1 comprises the amino acid sequence of SEQ ID NO:55;
(e) HVR-L2 comprises the amino acid sequence of SEQ ID NO:57; and
(f) HVR-L3 comprises the amino acid sequence of SEQ ID NO:59.

In some embodiments, the invention provides an isolated anti-hemagglutinin antibody comprising three light chain hypervariable regions (HVR-L1, HVR-L2, and LVR-L3), wherein:
(a) HVR-L1 comprises the amino acid sequence of SEQ ID NO:55;
(b) HVR-L2 comprises the amino acid sequence of SEQ ID NO:57; and
(c) HVR-L3 comprises the amino acid sequence of SEQ ID NO:59.

In some embodiments, the invention provides an isolated anti-hemagglutinin antibody comprising three heavy chain hypervariable regions (HVR-H1, HVR-H2, and HVR-H3), wherein:
(a) HVR-H1 comprises the amino acid sequence of SEQ ID NO:62;
(b) HVR-H2 comprises the amino acid sequence of SEQ ID NO:66; and
(c) HVR-H3 comprises the amino acid sequence of SEQ ID NO:76.

In some embodiments, the invention provides an isolated anti-hemagglutinin antibody comprising: at least one, two, and/or three light chain hypervariable region (HVR) sequences, wherein:
(a) HVR-L1 comprises the amino acid sequence of SEQ ID NO:55;

(b) HVR-L2 comprises the amino acid sequence of SEQ ID NO:57; and
(c) HVR-L3 comprises the amino acid sequence of SEQ ID NO:59.

In some embodiments, the invention provides an isolated anti-hemagglutinin antibody comprising: at least one, two, and/or three heavy chain hypervariable region (HVR) sequences, wherein:
(a) HVR-H1 comprises the amino acid sequence of SEQ ID NO:62;
(b) HVR-H2 comprises the amino acid sequence of SEQ ID NO:66; and
(c) HVR-H3 comprises the amino acid sequence of SEQ ID NO:76.

In some embodiments, an isolated anti-hemagglutinin antibody of the present invention comprises a heavy chain variable region and a light chain variable region, wherein the heavy chain variable region comprises the amino acid of SEQ ID NO:89, and the light chain variable region comprises the amino acid sequence of SEQ ID NO:78.

In some embodiments, an isolated anti-hemagglutinin antibody of the present invention comprises a light chain variable region comprising the amino acid sequence of SEQ ID NO:78.

In some embodiments, an isolated anti-hemagglutinin antibody of the present invention comprises a heavy chain variable region comprises the amino acid sequence of SEQ ID NO:89.

In some embodiments, an isolated anti-hemagglutinin antibody of the present invention comprises a heavy chain and a light chain, wherein the heavy chain comprises the amino acid sequence of SEQ ID NO:90, and the light chain comprises the amino acid sequence of SEQ ID NO:80.

In some embodiments, an isolated anti-hemagglutinin antibody of the present invention comprises a light chain comprising the amino acid sequence of SEQ ID NO:80.

In some embodiments, an isolated anti-hemagglutinin antibody of the present invention comprises a heavy chain comprising the amino acid sequence of SEQ ID NO:90.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:63;
(b) HVR-H2 comprises an amino acid sequence selected from the group consisting of SEQ ID NOs:67, 68, 69, 70, 71, 72, 73, and 74;
(c) HVR-H3 comprises the amino acid sequence of SEQ ID NO:77;
(d) HVR-L1 comprises the amino acid sequence of SEQ ID NO:56;
(e) HVR-L2 comprises the amino acid sequence of SEQ ID NO:58; and
(f) HVR-L3 comprises the amino acid sequence of SEQ ID NO:60.

In some embodiments, the invention provides an isolated anti-hemagglutinin antibody comprising: at least one, two, three, four, five and/or six hypervariable region (HVR) sequences, wherein:
(a) HVR-H1 comprises the amino acid sequence of SEQ ID NO:63;
(b) HVR-H2 comprises an amino acid sequence selected from the group consisting of SEQ ID NOs:67, 68, 69, 70, 71, 72, 73, and 74;
(c) HVR-H3 comprises the amino acid sequence of SEQ ID NO:77;
(d) HVR-L1 comprises the amino acid sequence of SEQ ID NO:56;
(e) HVR-L2 comprises the amino acid sequence of SEQ ID NO:58; and
(f) HVR-L3 comprises the amino acid sequence se of SEQ ID NO:60.

In some embodiments, the invention provides an isolated anti-hemagglutinin antibody comprising three light chain hypervariable regions (HVR-L1, HVR-L2, and LVR-L3), wherein:
(a) HVR-L1 comprises the amino acid sequence of SEQ ID NO:56;
(b) HVR-L2 comprises the amino acid sequence of SEQ ID NO:58; and
(c) HVR-L3 comprises the amino acid sequence of SEQ ID NO:60.

In some embodiments, the invention provides an isolated anti-hemagglutinin antibody comprising three heavy chain hypervariable regions (HVR-H1, HVR-H2, and HVR-H3), wherein:
(a) HVR-H1 comprises the amino acid sequence of SEQ ID NO:63;
(b) HVR-H2 comprises an amino acid sequence selected from the group consisting of SEQ ID NOs:67, 68, 69, 70, 71, 72, 73, and 74; and
(c) HVR-H3 comprises the amino acid sequence of SEQ ID NO:77.

In some embodiments, the invention provides an isolated anti-hemagglutinin antibody comprising: at least one, two, and/or three light chain hypervariable region (HVR) sequences, wherein:
(a) HVR-L1 comprises the amino acid sequence of SEQ ID NO:56;
(b) HVR-L2 comprises the amino acid sequence of SEQ ID NO:58; and
(c) HVR-L3 comprises the amino acid sequence of SEQ ID NO:60.

In some embodiments, the invention provides an isolated anti-hemagglutinin antibody comprising:
at least one, two, and/or three heavy chain hypervariable region (HVR) sequences, wherein:
(a) HVR-H1 comprises the amino acid sequence of SEQ ID NO:63;
(b) HVR-H2 comprises an amino acid sequence selected from the group consisting of SEQ ID NOs:67, 68, 69, 70, 71, 72, 73, and 74; and
(c) HVR-H3 comprises the amino acid sequence of SEQ ID NO:77.

In some embodiments, an isolated anti-hemagglutinin antibody of the present invention comprises a heavy chain variable region and a light chain variable region, wherein the heavy chain variable region comprises an amino acid sequence selected from the group consisting of SEQ ID NOs:92, 95, 97, 99, 101, 103, 105, and 107, and the light chain variable region comprises the amino acid sequence of SEQ ID NO:91.

In some embodiments, an isolated anti-hemagglutinin antibody of the present invention comprises a light chain variable region comprising the amino acid sequence of SEQ ID NO:91.

In some embodiments, an isolated anti-hemagglutinin antibody of the present invention comprises a heavy chain variable region comprises an amino acid sequence selected from the group consisting of SEQ ID NOs: 92, 95, 97, 99, 101, 103, 105, and 107.

In some embodiments, an isolated anti-hemagglutinin antibody of the present invention comprises a heavy chain and a light chain, wherein the heavy chain comprises an amino acid sequence selected from the group consisting of SEQ ID NOs:94, 96, 98, 100, 102, 104, 106, and 108, and the light chain comprises the amino acid sequence of SEQ ID NO:93.

In some embodiments, an isolated anti-hemagglutinin antibody of the present invention comprises a light chain comprising the amino acid sequence of SEQ ID NO:93.

In some embodiments, an isolated anti-hemagglutinin antibody of the present invention comprises a heavy chain comprising an amino acid sequence selected from the group consisting of SEQ ID NOs:94, 96, 98, 100, 102, 104, 106, and 108.

In some embodiments, the isolated anti-hemagglutinin antibody of the present invention is a monoclonal antibody. In some embodiments, the isolated anti-hemagglutinin antibody of the present invention specifically binds influenza B virus hemagglutinin. In some embodiments, the isolated anti-hemagglutinin antibody is an isolated anti-hemagglutinin monoclonal antibody that specifically binds influenza B virus hemagglutinin.

The invention also provides isolated nucleic acids encoding an anti-hemagglutinin antibody of the present invention. The invention also provides vectors comprising a nucleic acid encoding an anti-hemagglutinin antibody of the present invention. The invention also provides host cells comprising a nucleic acid or a vector of the present invention. A vector can be of any type, for example, a recombinant vector such as an expression vector. Any of a variety of host cells can be used. In one embodiment, a host cell is a prokaryotic cell, for example, *E. coli*. In another embodiment, a host cell is a eukaryotic cell, for example, a mammalian cell, such as a Chinese Hamster Ovary (CHO) cell.

The invention further provides a method of producing an anti-hemagglutinin antibody of the present invention. For example, the invention provides methods for making an anti-hemagglutinin antibody (which, as defined herein, includes full length antibody and fragments thereof), the method comprising expressing in a suitable host cell a recombinant vector of the invention encoding the anti-hemagglutinin antibody or fragments thereof so that the antibody or fragments thereof are produced. In some embodiments, the method comprises culturing a host cell comprising nucleic acid encoding an anti-hemagglutinin antibody of the present invention (or fragments thereof) so that the nucleic acid is expressed. The method may further comprise recovering the anti-hemagglutinin antibody or fragments thereof from the host cell culture or the host cell culture medium.

The invention also provides a pharmaceutical formulation comprising an anti-hemagglutinin antibody of the present invention and a pharmaceutically acceptable carrier. The pharmaceutical formulation may further comprise an additional therapeutic agent (e.g., a neuraminidase inhibitor, such as oseltamivir or zanamivir; another antibody, such as another anti-hemagglutinin antibody or an anti-M2 antibody; etc).

The invention also provides compositions comprising an anti-hemagglutinin antibody of the present invention. The composition may further comprise an additional therapeutic agent (e.g., a neuraminidase inhibitor, such as oseltamivir or zanamivir; another antibody, such as another anti-hemagglutinin antibody or an anti-M2 antibody; etc).

The invention also provides a composition comprising an anti-hemagglutinin antibody of the present invention for use in preventing influenza B virus infection. In some embodiments, the invention provides a pharmaceutical composition comprising an anti-hemagglutinin antibody of the present invention for use in preventing influenza B virus infection. The invention further provides a composition comprising an anti-hemagglutinin antibody of the present invention for use in treating influenza B virus infection. In some embodiments, the invention provides a pharmaceutical composition comprising an anti-hemagglutinin antibody of the present invention for use in treating influenza B virus infection. The invention further provides a composition comprising an anti-hemagglutinin antibody of the present invention for use in inhibiting influenza B virus infection. In some embodiments, the invention provides a pharmaceutical composition comprising an anti-hemagglutinin antibody of the present invention for use in inhibiting influenza B virus infection.

Compositions comprising an anti-hemagglutinin antibody of the present invention may also be used in the manufacture of a medicament. The medicament may be for use in the inhibition, treatment, or prevention of influenza B virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

The invention also provides a method for inhibiting influenza B virus infection, the method comprising administering to a subject in need thereof an effective amount of a composition comprising an anti-hemagglutinin antibody of the present invention, thereby inhibiting influenza B virus infection. The invention also provides a method for treating influenza B virus infection, the method comprising administering to a subject in need thereof an effective amount of a composition comprising an anti-hemagglutinin antibody of the present invention, thereby treating influenza B virus infection. The invention also provides a method for preventing influenza B virus infection, the method comprising administering to a subject in need thereof an effective amount of a composition comprising an anti-hemagglutinin antibody of the present invention, thereby preventing influenza B virus infection.

The invention also provides a method for inhibiting, treating, or preventing influenza B virus infection, the method comprising administering to a patient in need thereof an effective amount of a composition comprising an anti-hemagglutinin antibody of the present invention, and administering to the patient an effective amount of an additional therapeutic agent, thereby inhibiting, treating, or preventing influenza B virus infection. In some embodiments, the additional therapeutic agent is a neuraminidase inhibitor, such as oseltamivir or zanamivir. In other embodiments, the additional therapeutic agent is another anti-hemagglutinin antibody. In yet other embodiments, the additional therapeutic agent is an anti-M2 antibody. In various aspects of such combination treatments, the therapeutic agents are administered at about the same time, are administered together, or are administered sequentially or consecutively. In particular embodiments, an anti-neuraminidase inhibitor is administered prior to the administration of an anti-hemagglutinin antibody of the present invention. In some embodiments, the anti-influenza B virus hemagglutinin antibodies of the present invention are effective at neutralizing, inhibiting, treating, or preventing influenza B virus infection from influenza B virus strains of different lineages, including ancestral, Yamagata, and Victoria lineages.

In another aspect, the invention provides use of an anti-hemagglutinin antibody of the present invention in the manufacture of a medicament. The medicament may be for use in the inhibition, treatment, or prevention of influenza B virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of a nucleic acid of the invention in the manufacture of a medicament. The medicament may be for use in the inhibition, treatment, or prevention of influenza B virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of an expression vector of the invention in the manufacture of a medicament. The medicament may be for use in the inhibition, treatment, or prevention of influenza B virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of a host cell of the invention in the manufacture of a medicament. The medicament may be for use in the inhibition, treatment, or prevention of influenza B virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of an article of manufacture of the invention in the manufacture of a medicament. The medicament may be for use in the inhibition, treatment, or prevention of influenza B virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of a kit of the invention in the manufacture of a medicament. The medicament may be for use in the inhibition, treatment, or prevention of influenza B virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In various aspects, an anti-hemagglutinin antibody of the present invention binds hemagglutinin of influenza B virus. In other aspects, an anti-hemagglutinin antibody of the present invention binds hemagglutinin and neutralizes influenza B virus. In some embodiments, an anti-hemagglutinin antibody of the present invention neutralizes influenza B virus in vitro, in vivo, or in vitro and in vivo.

BRIEF DESCRIPTION OF THE FIGURES

FIG. 13 sets forth the amino acid sequences of light chain and heavy chain hypervariable regions of anti-influenza B virus antibodies of the present invention.

FIG. 14 sets forth the amino acid sequences of light chain variable region, heavy chain variable region, light chain, and heavy chain of mAb 34B5A.

FIG. 15 sets forth the amino acid sequences of light chain variable region, heavy chain variable region, light chain, and heavy chain of mAb 34B5B.

FIG. 16 sets forth the amino acid sequences of light chain variable region, heavy chain variable region, light chain, and heavy chain of mAb 34B5C.

FIG. 17 sets forth the amino acid sequences of light chain variable region, heavy chain variable region, light chain, and heavy chain of mAb 33F8.

FIG. 18 sets forth the amino acid sequences of light chain variable region, heavy chain variable region, light chain, and heavy chain of mAb 46B8A.

FIG. 19 sets forth the amino acid sequences of light chain variable region, heavy chain variable region, light chain, and heavy chain of mAb 46B8B.

FIG. 20 sets forth the amino acid sequences of light chain variable region, heavy chain variable region, light chain, and heavy chain of mAb 46B8C.

FIG. 21 sets forth the amino acid sequences of light chain variable region, heavy chain variable region, light chain, and heavy chain of mAb 46B8D.

FIG. 22 sets forth the amino acid sequences of light chain variable region, heavy chain variable region, light chain, and heavy chain of mAb 46B8E.

FIG. 23 sets forth the amino acid sequences of light chain variable region, heavy chain variable region, light chain, and heavy chain of mAb 46B8F.

FIG. 24 sets forth the amino acid sequences of light chain variable region, heavy chain variable region, light chain, and heavy chain of mAb 46B8G.

FIG. 25 sets forth the amino acid sequences of light chain variable region, heavy chain variable region, light chain, and heavy chain of mAb 46B8H.

DETAILED DESCRIPTION OF EMBODIMENTS OF THE INVENTION

I. Definitions

Figure 1A:
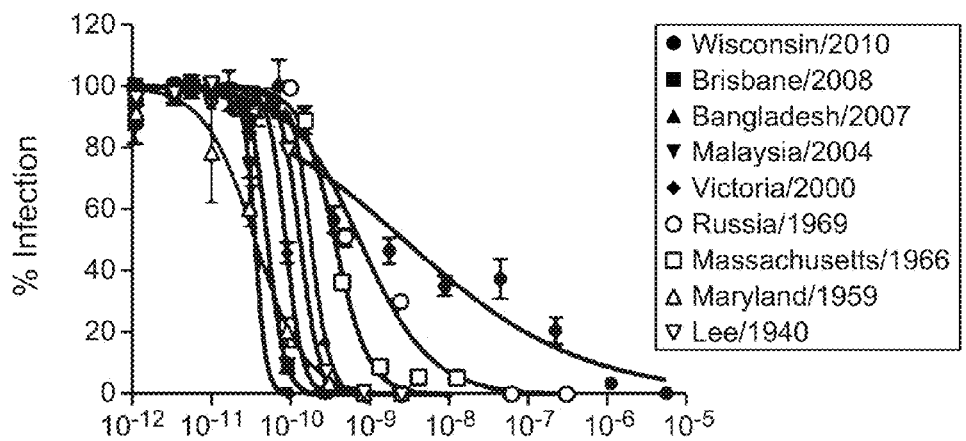
FIGS. 1A and 1B set forth data showing in vitro neutralization of various influenza B virus isolates by monoclonal antibody 34B5A and monoclonal antibody 33F8, respectively.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-hemagglutinin antibody" and "an antibody that binds to hemagglutinin" refer to an antibody that binds hemagglutinin with sufficient affinity such that the antibody is useful as a diagnostic and/or therapeutic agent in targeting hemagglutinin, including targeting hemagglutinin of influenza virus. In one embodiment, the extent of binding of an anti-hemagglutinin antibody to an unrelated, non-hemagglutinin protein is less than about 10% of the binding of the antibody to hemagglutinin as measured, e.g., by a radioimmunoassay (RIA). In certain embodiments, an antibody that binds to hemagglutinin has a dissociation constant (Kd) of ≤1 µM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$ M, e.g., from $10^{-9}$M to $10^{-13}$ M). In certain embodiments, an anti-hemagglutinin antibody binds to an epitope of hemagglutinin of influenza B virus that is conserved among hemagglutinin from different strains, subtypes, and isolates of influenza B viruses, such as that of hemagglutinin of influenza B viruses of ancestral, Victoria, or Yamagata lineages.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. An antibody fragment also refers to a molecule other than an intact antibody that comprises a portion of an intact antibody that binds hemagglutinin and neutralizes influenza A virus. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-hemagglutinin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "hemagglutinin," as used herein, refers to any native hemagglutinin from any influenza virus source, unless otherwise indicated. The term encompasses "full-length," unprocessed hemagglutinin as well as any form of hemagglutinin that results from processing in an influenza virus or an influenza virus-infected cell. The term also encompasses naturally occurring variants of hemagglutinin, e.g., splice variants or allelic variants. The amino acid sequences of exemplary hemagglutinin proteins from various influenza B virus strains or lineages are readily available in the art.

As used herein, "treatment" (and grammatical variations thereof such as "treat" or "treating") refers to clinical intervention in an attempt to alter the natural course of the individual being treated, and can be performed either for prophylaxis or during the course of clinical pathology.

Desirable effects of treatment include, but are not limited to, preventing occurrence or recurrence of disease (e.g., preventing occurrence or recurrence of influenza B virus infection), reduction (e.g., reducing) or alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on anti-hemagglutinin antibodies and uses thereof. In certain embodiments, antibodies that bind to hemagglutinin are provided. Antibodies of the invention are useful, e.g., for the diagnosis, treatment, or prevention of influenza A virus infection.

A. Exemplary Anti-Hemagglutinin Antibodies

In one aspect, the invention provides isolated antibodies that bind to hemagglutinin. In certain embodiments, an anti-hemagglutinin antibody of the present invention binds hemagglutinin, binds hemagglutinin from influenza B virus, binds hemagglutinin from the Yamagata lineage of influenza B viruses, binds hemagglutinin from the Victoria lineage of influenza B viruses, binds hemagglutinin from ancestral lineages of influenza B virus, or binds hemagglutinin from the Yamagata lineage, the Victoria lineage, and ancestral lineages of influenza B virus. In other embodiments, an anti-hemagglutinin antibody of the present invention neutralizes influenza B virus in vitro. In other embodiments, an anti-hemagglutinin antibody of the present invention neutralizes influenza B virus in vivo. In yet other embodiments, an anti-hemagglutinin antibody of the present invention reduces influenza B virus infection, prevents influenza B virus infection, inhibits influenza B virus infection, or treats influenza B virus infection. In some embodiments, an anti-hemagglutinin antibody of the present invention prevents, inhibits, or reduces hemagglutinin-mediated fusion between influenza virus membrane and infected cell endosomal membranes (thus preventing, inhibiting, or reducing viral RNA entry into the infected cell cytoplasm, thus preventing, inhibiting, or reducing further propagation of influenza virus infection.)

In one aspect, the invention provides an anti-hemagglutinin antibody comprising at least one, two, three, four, five, or six HVRs selected from (a) HVR-H1 comprising the amino acid sequence of SEQ ID NO:61; (b) HVR-H2 comprising the amino acid sequence of SEQ ID NO:64; (c) HVR-H3 comprising the amino acid sequence of SEQ ID NO:75; (d) HVR-L1 comprising the amino acid sequence of SEQ ID NO:55; (e) HVR-L2 comprising the amino acid sequence of SEQ ID NO:57; and (f) HVR-L3 comprising the amino acid sequence of SEQ ID NO:59.

In one aspect, the invention provides an anti-hemagglutinin antibody comprising at least one, two, three, four, five, or six HVRs selected from (a) HVR-H1 comprising the amino acid sequence of SEQ ID NO:61; (b) HVR-H2 comprising the amino acid sequence of SEQ ID NO:65; (c) HVR-H3 comprising the amino acid sequence of SEQ ID NO:75; (d) HVR-L1 comprising the amino acid sequence of SEQ ID NO:55; (e) HVR-L2 comprising the amino acid sequence of SEQ ID NO:57; and (f) HVR-L3 comprising the amino acid sequence of SEQ ID NO:59.

In one aspect, the invention provides an antibody comprising at least one, at least two, or all three VH HVR sequences selected from (a) HVR-H1 comprising the amino acid sequence of SEQ ID NO:61; (b) HVR-H2 comprising the amino acid sequence of SEQ ID NO:64; and (c) HVR-H3 comprising the amino acid sequence of SEQ ID NO:75.

In one aspect, the invention provides an antibody comprising at least one, at least two, or all three VH HVR sequences selected from (a) HVR-H1 comprising the amino acid sequence of SEQ ID NO:61; (b) HVR-H2 comprising the amino acid sequence of SEQ ID NO:65; and (c) HVR-H3 comprising the amino acid sequence of SEQ ID NO:75.

In another aspect, the invention provides an antibody comprising at least one, at least two, or all three VL HVR sequences selected from (a) HVR-L1 comprising the amino acid sequence of SEQ ID NO:55; (b) HVR-L2 comprising the amino acid sequence of SEQ ID NO:57; and (c) HVR-L3 comprising the amino acid sequence of SEQ ID NO:59.

In another aspect, the invention provides an antibody comprising (a) HVR-H1 comprising the amino acid sequence of SEQ ID NO:61; (b) HVR-H2 comprising the amino acid sequence of SEQ ID NO:64; (c) HVR-H3 comprising the amino acid sequence of SEQ ID NO:75; (d) HVR-L1 comprising the amino acid sequence of SEQ ID NO:55; (e) HVR-L2 comprising the amino acid sequence of SEQ ID NO:57; and (f) HVR-L3 comprising the amino acid sequence selected from SEQ ID NO:59.

In another aspect, the invention provides an antibody comprising (a) HVR-H1 comprising the amino acid sequence of SEQ ID NO:61; (b) HVR-H2 comprising the amino acid sequence of SEQ ID NO:65; (c) HVR-H3 comprising the amino acid sequence of SEQ ID NO:75; (d) HVR-L1 comprising the amino acid sequence of SEQ ID NO:55; (e) HVR-L2 comprising the amino acid sequence of SEQ ID NO:57; and (f) HVR-L3 comprising the amino acid sequence selected from SEQ ID NO:59.

In another aspect, the invention provides an antibody comprising a heavy chain variable region comprising an amino acid sequence selected from the group consisting of SEQ ID NOs:79 and 83.

In another aspect, the invention provides an antibody comprising a light chain variable region comprising an amino acid sequence selected from the group consisting of SEQ ID NOs:78, 82, and 86.

In another aspect, the invention provides an antibody comprising a heavy chain variable region comprising an amino acid sequence selected from the group consisting of SEQ ID NOs:79 and 83 and a light chain variable region comprising an amino acid sequence selected from the group consisting of SEQ ID NOs:78, 82 and 86.

In one embodiment, the invention provides an antibody comprising a heavy chain variable region comprising the amino acid sequence of SEQ ID NO:79 and a light chain variable region comprising the amino acid sequence of SEQ ID NO:78.

In one embodiment, the invention provides an antibody comprising a heavy chain variable region comprising the amino acid sequence of SEQ ID NO:83 and a light chain variable region comprising the amino acid sequence of SEQ ID NO:82.

In one embodiment, the invention provides an antibody comprising a heavy chain variable region comprising the amino acid sequence of SEQ ID NO:83 and a light chain variable region comprising the amino acid sequence of SEQ ID NO:86.

In another aspect, the invention provides an antibody comprising a heavy chain comprising an amino acid sequence selected from the group consisting of SEQ ID NOs:81, 85, and 88.

In another aspect, the invention provides an antibody comprising a light chain comprising an amino acid sequence selected from the group consisting of SEQ ID NOs:80, 84, and 87.

In another aspect, the invention provides an antibody comprising a heavy chain comprising an amino acid sequence selected from the group consisting of SEQ ID NOs:81, 85, and 88 and a light chain comprising an amino acid sequence selected from the group consisting of SEQ ID NOs:80, 84, and 87.

In one embodiment, the invention provides an antibody comprising a heavy chain comprising the amino acid sequence of SEQ ID NO:81 and a light chain comprising the amino acid sequence of SEQ ID NO:80.

In one embodiment, the invention provides an antibody comprising a heavy chain comprising the amino acid sequence SEQ ID NO:85 and a light chain comprising the amino acid sequence selected from the group consisting of SEQ ID NO:84.

In one embodiment, the invention provides an antibody comprising a heavy chain comprising the amino acid sequence of SEQ ID NO:88 and a light chain comprising the amino acid sequence of SEQ ID NO:87.

In one aspect, the invention provides an anti-hemagglutinin antibody comprising at least one, two, three, four, five, or six HVRs selected from (a) HVR-H1 comprising the amino acid sequence of SEQ ID NO:62; (b) HVR-H2 comprising the amino acid sequence of SEQ ID NO:66; (c) HVR-H3 comprising the amino acid sequence of SEQ ID NO:76; (d) HVR-L1 comprising the amino acid sequence of SEQ ID NO:55; (e) HVR-L2 comprising the amino acid sequence of SEQ ID NO:57; and (f) HVR-L3 comprising the amino acid sequence of SEQ ID NO:59.

In one aspect, the invention provides an antibody comprising at least one, at least two, or all three VH HVR sequences selected from (a) HVR-H1 comprising the amino acid sequence of SEQ ID NO:62; (b) HVR-H2 comprising the amino acid sequence of SEQ ID NO:66; and (c) HVR-H3 comprising the amino acid sequence of SEQ ID NO:76.

In another aspect, the invention provides an antibody comprising at least one, at least two, or all three VL HVR sequences selected from (a) HVR-L1 comprising the amino acid sequence of SEQ ID NO:55; (b) HVR-L2 comprising the amino acid sequence of SEQ ID NO:57; and (c) HVR-L3 comprising the amino acid sequence of SEQ ID NO:59.

In another aspect, the invention provides an antibody comprising (a) HVR-H1 comprising the amino acid sequence of SEQ ID NO:62; (b) HVR-H2 comprising the amino acid sequence of SEQ ID NO:66; (c) HVR-H3 comprising the amino acid sequence of SEQ ID NO:76; (d) HVR-L1 comprising the amino acid sequence of SEQ ID NO:55; (e) HVR-L2 comprising the amino acid sequence of SEQ ID NO:57; and (f) HVR-L3 comprising the amino acid sequence selected from SEQ ID NO:59.

In another aspect, the invention provides an antibody comprising a heavy chain variable region comprising the amino acid sequence of SEQ ID NO:89.

In another aspect, the invention provides an antibody comprising a light chain variable region comprising the amino acid sequence of SEQ ID NO:78.

In one embodiment, the invention provides an antibody comprising a heavy chain variable region comprising the amino acid sequence of SEQ ID NO:89 and a light chain variable region comprising the amino acid sequence of SEQ ID NO:78.

In one embodiment, the invention provides an antibody comprising a heavy chain comprising the amino acid sequence of SEQ ID NO:90 and a light chain comprising the amino acid sequence of SEQ ID NO:80.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising an amino acid sequence selected from the group consisting of SEQ ID NOs:67, 68, 69, 70, 71, 72, 73, and 74; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising the amino acid sequence of SEQ ID NO:67; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising the amino acid sequence of SEQ ID NO:68; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising the amino acid sequence of SEQ ID NO:69; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising the amino acid sequence of SEQ ID NO:70; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising the amino acid sequence of SEQ ID NO:71; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising the amino acid sequence of SEQ ID NO:72; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising the amino acid sequence of SEQ ID NO:73; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an anti-hemagglutinin antibody comprising at least one, two, three, four, five, or six HVRs selected from (a) HVR-H1 comprising the amino acid sequence of SEQ ID NO:63; (b) HVR-H2 comprising the amino acid sequence of SEQ ID NO:74; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence of SEQ ID NO:60.

In one aspect, the invention provides an antibody comprising at least one, at least two, or all three VH HVR sequences selected from (a) HVR-H1 comprising the amino acid sequence of SEQ ID NO:63; (b) HVR-H2 comprising the amino acid sequence of SEQ ID NO:67; and (c) HVR-H3 comprising the amino acid sequence of SEQ ID NO:77.

In one aspect, the invention provides an antibody comprising at least one, at least two, or all three VH HVR sequences selected from (a) HVR-H1 comprising the amino acid sequence of SEQ ID NO:63; (b) HVR-H2 comprising the amino acid sequence of SEQ ID NO:68; and (c) HVR-H3 comprising the amino acid sequence of SEQ ID NO:77.

In one aspect, the invention provides an antibody comprising at least one, at least two, or all three VH HVR sequences selected from (a) HVR-H1 comprising the amino acid sequence of SEQ ID NO:63; (b) HVR-H2 comprising the amino acid sequence of SEQ ID NO:69; and (c) HVR-H3 comprising the amino acid sequence of SEQ ID NO:77.

In one aspect, the invention provides an antibody comprising at least one, at least two, or all three VH HVR sequences selected from (a) HVR-H1 comprising the amino acid sequence of SEQ ID NO:63; (b) HVR-H2 comprising the amino acid sequence of SEQ ID NO:70; and (c) HVR-H3 comprising the amino acid sequence of SEQ ID NO:77.

In one aspect, the invention provides an antibody comprising at least one, at least two, or all three VH HVR sequences selected from (a) HVR-H1 comprising the amino acid sequence of SEQ ID NO:63; (b) HVR-H2 comprising the amino acid sequence of SEQ ID NO:71; and (c) HVR-H3 comprising the amino acid sequence of SEQ ID NO:77.

In one aspect, the invention provides an antibody comprising at least one, at least two, or all three VH HVR sequences selected from (a) HVR-H1 comprising the amino acid sequence of SEQ ID NO:63; (b) HVR-H2 comprising the amino acid sequence of SEQ ID NO:72; and (c) HVR-H3 comprising the amino acid sequence of SEQ ID NO:77.

In one aspect, the invention provides an antibody comprising at least one, at least two, or all three VH HVR sequences selected from (a) HVR-H1 comprising the amino acid sequence of SEQ ID NO:63; (b) HVR-H2 comprising the amino acid sequence of SEQ ID NO:73; and (c) HVR-H3 comprising the amino acid sequence of SEQ ID NO:77.

In one aspect, the invention provides an antibody comprising at least one, at least two, or all three VH HVR sequences selected from (a) HVR-H1 comprising the amino acid sequence of SEQ ID NO:63; (b) HVR-H2 comprising the amino acid sequence of SEQ ID NO:74; and (c) HVR-H3 comprising the amino acid sequence of SEQ ID NO:77.

In another aspect, the invention provides an antibody comprising at least one, at least two, or all three VL HVR sequences selected from (a) HVR-L1 comprising the amino acid sequence of SEQ ID NO:56; (b) HVR-L2 comprising the amino acid sequence of SEQ ID NO:58; and (c) HVR-L3 comprising the amino acid sequence of SEQ ID NO:60.

In another aspect, the invention provides an antibody comprising (a) HVR-H1 comprising the amino acid sequence of SEQ ID NO:63; (b) HVR-H2 comprising the amino acid sequence of SEQ ID NO:67; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence selected from SEQ ID NO:60.

In another aspect, the invention provides an antibody comprising (a) HVR-H1 comprising the amino acid sequence of SEQ ID NO:63; (b) HVR-H2 comprising the amino acid sequence of SEQ ID NO:68; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence selected from SEQ ID NO:60.

In another aspect, the invention provides an antibody comprising (a) HVR-H1 comprising the amino acid sequence of SEQ ID NO:63; (b) HVR-H2 comprising the amino acid sequence of SEQ ID NO:69; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence selected from SEQ ID NO:60.

In another aspect, the invention provides an antibody comprising (a) HVR-H1 comprising the amino acid sequence of SEQ ID NO:63; (b) HVR-H2 comprising the amino acid sequence of SEQ ID NO:70; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence selected from SEQ ID NO:60.

In another aspect, the invention provides an antibody comprising (a) HVR-H1 comprising the amino acid sequence of SEQ ID NO:63; (b) HVR-H2 comprising the amino acid sequence of SEQ ID NO:71; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence selected from SEQ ID NO:60.

In another aspect, the invention provides an antibody comprising (a) HVR-H1 comprising the amino acid sequence of SEQ ID NO:63; (b) HVR-H2 comprising the amino acid sequence of SEQ ID NO:72; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence selected from SEQ ID NO:60.

In another aspect, the invention provides an antibody comprising (a) HVR-H1 comprising the amino acid sequence of SEQ ID NO:63; (b) HVR-H2 comprising the amino acid sequence of SEQ ID NO:73; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence selected from SEQ ID NO:60.

In another aspect, the invention provides an antibody comprising (a) HVR-H1 comprising the amino acid sequence of SEQ ID NO:63; (b) HVR-H2 comprising the amino acid sequence of SEQ ID NO:74; (c) HVR-H3 comprising the amino acid sequence of SEQ ID NO:77; (d) HVR-L1 comprising the amino acid sequence of SEQ ID NO:56; (e) HVR-L2 comprising the amino acid sequence of SEQ ID NO:58; and (f) HVR-L3 comprising the amino acid sequence selected from SEQ ID NO:60.

In another aspect, the invention provides an antibody comprising a heavy chain variable region comprising an amino acid sequence selected from the group consisting of SEQ ID NOs:92, 95, 97, 99, 101, 103, 105, and 107.

In another aspect, the invention provides an antibody comprising a light chain variable region comprising the amino acid sequence of SEQ ID NO:91.

In another aspect, the invention provides an antibody comprising a heavy chain variable region comprising an amino acid sequence selected from the group consisting of SEQ ID NOs: 92, 95, 97, 99, 101, 103, 105, and 107 and a light chain variable region comprising the amino acid sequence of SEQ ID NO:91.

In one embodiment, the invention provides an antibody comprising a heavy chain variable region comprising the amino acid sequence of SEQ ID NO:92 and a light chain variable region comprising the amino acid sequence of SEQ ID NO:91.

In one embodiment, the invention provides an antibody comprising a heavy chain variable region comprising the amino acid sequence of SEQ ID NO:95 and a light chain variable region comprising the amino acid sequence of SEQ ID NO:91.

In one embodiment, the invention provides an antibody comprising a heavy chain variable region comprising the amino acid sequence of SEQ ID NO:97 and a light chain variable region comprising the amino acid sequence of SEQ ID NO:91.

In one embodiment, the invention provides an antibody comprising a heavy chain variable region comprising the amino acid sequence of SEQ ID NO:99 and a light chain variable region comprising the amino acid sequence of SEQ ID NO:91.

In one embodiment, the invention provides an antibody comprising a heavy chain variable region comprising the amino acid sequence of SEQ ID NO:101 and a light chain variable region comprising the amino acid sequence of SEQ ID NO:91.

In one embodiment, the invention provides an antibody comprising a heavy chain variable region comprising the amino acid sequence of SEQ ID NO:103 and a light chain variable region comprising the amino acid sequence of SEQ ID NO:91.

In one embodiment, the invention provides an antibody comprising a heavy chain variable region comprising the amino acid sequence of SEQ ID NO:105 and a light chain variable region comprising the amino acid sequence of SEQ ID NO:91.

In one embodiment, the invention provides an antibody comprising a heavy chain variable region comprising the amino acid sequence of SEQ ID NO:107 and a light chain variable region comprising the amino acid sequence of SEQ ID NO:91.

In another aspect, the invention provides an antibody comprising a heavy chain comprising an amino acid sequence selected from the group consisting of SEQ ID NOs:94, 96, 98, 100, 102, 104, 106, and 108.

In another aspect, the invention provides an antibody comprising a light chain comprising the amino acid sequence of SEQ ID NO:93.

In another aspect, the invention provides an antibody comprising a heavy chain comprising an amino acid sequence selected from the group consisting of SEQ ID NOs: 94, 96, 98, 100, 102, 104, 106, and 108 and a light chain comprising the amino acid sequence of SEQ ID NO:93.

In one embodiment, the invention provides an antibody comprising a heavy chain comprising the amino acid sequence of SEQ ID NO:94 and a light chain comprising the amino acid sequence of SEQ ID NO:93.

In one embodiment, the invention provides an antibody comprising a heavy chain comprising the amino acid sequence of SEQ ID NO:96 and a light chain comprising the amino acid sequence of SEQ ID NO:93.

In one embodiment, the invention provides an antibody comprising a heavy chain comprising the amino acid sequence of SEQ ID NO:98 and a light chain comprising the amino acid sequence of SEQ ID NO:93.

In one embodiment, the invention provides an antibody comprising a heavy chain comprising the amino acid sequence of SEQ ID NO:100 and a light chain comprising the amino acid sequence of SEQ ID NO:93.

In one embodiment, the invention provides an antibody comprising a heavy chain comprising the amino acid sequence of SEQ ID NO:102 and a light chain comprising the amino acid sequence of SEQ ID NO:93.

In one embodiment, the invention provides an antibody comprising a heavy chain comprising the amino acid sequence of SEQ ID NO:104 and a light chain comprising the amino acid sequence of SEQ ID NO:93.

In one embodiment, the invention provides an antibody comprising a heavy chain comprising the amino acid sequence of SEQ ID NO:106 and a light chain comprising the amino acid sequence of SEQ ID NO:93.

In one embodiment, the invention provides an antibody comprising a heavy chain comprising the amino acid sequence of SEQ ID NO:108 and a light chain comprising the amino acid sequence of SEQ ID NO:93.

In any of the above embodiments, an anti-hemagglutinin antibody of the present invention is humanized. In one embodiment, an anti-hemagglutinin antibody comprises HVRs as in any of the above embodiments, and further comprises an acceptor human framework, e.g., a human immunoglobulin framework or a human consensus framework.

In another aspect, an anti-hemagglutinin antibody of the present comprises a heavy chain variable domain (VH) sequence having at least 90%, 91%, 92%, 93%, 94%, 95%, 96%, 97%, 98%, 99%, or 100% sequence identity to an amino acid sequence selected from the group consisting of SEQ ID NOs:79, 83, 89, 92, 95, 97, 99, 101, 103, 105, and 107. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-hemagglutinin antibody comprising that sequence retains the ability to bind to hemagglutinin. In certain embodiments, a total of 1 to 10 amino acids have been substituted, inserted and/or deleted in SEQ ID NO:79, 83, 89, 92, 95, 97, 99, 101, 103, 105, or 107. In certain embodiments, substitutions, insertions, or deletions occur in regions outside the HVRs (i.e., in the FRs). Optionally, the anti hemagglutinin antibody comprises the VH sequence in SEQ ID NO:79, 83, 89, 92, 95, 97, 99, 101, 103, 105, or 107, including post-translational modifications of that sequence.

In another aspect, an anti-hemagglutinin antibody is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from the group consisting of SEQ ID NOs:78, 82, 86, and 91. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-hemagglutinin antibody comprising that sequence retains the ability to bind to hemagglutinin. In certain embodiments, a total of 1 to 10 amino acids have been substituted, inserted and/or deleted in SEQ ID NO:78, 82, 86, or 91. In certain embodiments, the substitutions, insertions, or deletions occur in regions outside the HVRs (i.e., in the FRs). Optionally, the anti-hemagglutinin antibody comprises the VL sequence in SEQ ID NO:78, 82, 86, or 91, including post-translational modifications of that sequence.

In another aspect, an anti-hemagglutinin antibody is provided, wherein the antibody comprises a VH as in any of the embodiments provided above, and a VL as in any of the embodiments provided above. In one embodiment, the antibody comprises the VH and VL sequences in SEQ ID NO:79, 83, 89, 92, 95, 97, 99, 101, 103, 105, or 107 and SEQ ID NO:78, 82, 86, or 91, respectively, including post-translational modifications of those sequences.

In a further aspect, the invention provides an antibody that binds to the same epitope as an anti-hemagglutinin antibody provided herein. For example, in certain embodiments, an antibody is provided that binds to the same epitope as an anti-hemagglutinin antibody comprising a VH sequence of SEQ ID NO:79 and a VL sequence of SEQ ID NO:78; a VH sequence of SEQ ID NO:83 and a VL sequence of SEQ ID NO:82; a VH sequence of SEQ ID NO:83 and a VL sequence of SEQ ID NO:86; a VH sequence of SEQ ID NO:89 and a VL sequence of SEQ ID NO:78; a VH sequence of SEQ ID NO:92 and a VL sequence of SEQ ID NO:91; a VH sequence of SEQ ID NO:95 and a VL sequence of SEQ ID NO:91; a VH sequence of SEQ ID NO:97 and a VL sequence of SEQ ID NO:91; a VH sequence of SEQ ID NO:99 and a VL sequence of SEQ ID NO:91; a VH sequence of SEQ ID NO:101 and a VL sequence of SEQ ID NO:91; a VH sequence of SEQ ID NO:103 and a VL sequence of SEQ ID NO:91; a VH sequence of SEQ ID NO:105 and a VL sequence of SEQ ID NO:91; a VH sequence of SEQ ID NO:107 and a VL sequence of SEQ ID NO:91.

In a further aspect of the invention, an anti-hemagglutinin antibody according to any of the above embodiments is a monoclonal antibody, including a chimeric, humanized, or human antibody. In one embodiment, an anti-hemagglutinin antibody is an antibody fragment, e.g., a Fv, Fab, Fab', scFv, diabody, or F(ab')$_2$ fragment. In another embodiment, the antibody is a full length antibody, e.g., an intact, e.g., IgG1 antibody or other antibody class or isotype as defined herein.

In a further aspect, an anti-hemagglutinin antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIA- CORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al., *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art or using techniques described herein. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAb® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for hemagglutinin and the other is for any other antigen. In certain embodiments, bispecific antibodies may bind to two different epitopes of hemagglutinin. Bispecific antibodies may also be used to localize cytotoxic agents to cells which express hemagglutinin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to hemagglutinin as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al., in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-hemagglutinin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-hemagglutinin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-hemagglutinin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology,* Vol. 248 (B. K. C. Lo, ed., Humana Press, Totowa, N.J.), pp. 255-268 (2003).

C. Assays

Anti-hemagglutinin antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes for binding of hemagglutinin with any anti-hemagglutinin antibody described herein. In certain embodiments, such a competing antibody binds to the same epitope (e.g., a linear or a conformational epitope) that is bound by an anti-hemagglutinin antibody described here (e.g., an anti-hemagglutinin antibody comprising a VH sequence of SEQ ID NO:79 and a VL sequence of SEQ ID NO:78; a VH sequence of SEQ ID NO:83 and a VL sequence of SEQ ID NO:82; a VH sequence of SEQ ID NO:83 and a VL sequence of SEQ ID NO:86; a VH sequence of SEQ ID NO:89 and a VL sequence of SEQ ID NO:78; a VH sequence of SEQ ID NO:92 and a VL sequence of SEQ ID NO:91; a VH sequence of SEQ ID NO:95 and a VL sequence of SEQ ID NO:91; a VH sequence of SEQ ID NO:97 and a VL sequence of SEQ ID NO:91; a VH sequence of SEQ ID NO:99 and a VL sequence of SEQ ID NO:91; a VH sequence of SEQ ID NO:101 and a VL sequence of SEQ ID NO:91; a VH sequence of SEQ ID NO:103 and a VL sequence of SEQ ID NO:91; a VH sequence of SEQ ID NO:105 and a VL sequence of SEQ ID NO:91; a VH sequence of SEQ ID NO:107 and a VL sequence of SEQ ID NO:91. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized hemagglutinin is incubated in a solution comprising a first labeled antibody that binds to hemagglutinin and a second unlabeled antibody that is being tested for its ability to compete with the first antibody for binding to hemagglutinin. The second antibody may be present in a hybridoma supernatant. As a control, immobilized hemagglutinin is incubated in a solution comprising the first labeled antibody but not the second unlabeled antibody. After incubation under conditions permissive for binding of the first antibody to hemagglutinin, excess unbound antibody is removed, and the amount of label associated with immobilized hemagglutinin is measured. If the amount of label associated with immobilized hemagglutinin is substantially reduced in the test sample relative to the control sample, then that indicates that the second antibody is competing with the first antibody for binding to hemagglutinin. See Harlow and Lane (1988) *Antibodies: A Laboratory Manual* ch.14 (Cold Spring Harbor Laboratory, Cold Spring Harbor, N.Y.).

2. Activity Assays

In one aspect, assays are provided for identifying anti-hemagglutinin antibodies and fragments thereof having biological activity. Biological activity may include, e.g., specifically binding to influenza B virus hemagglutinin, neutralizing influenza B virus, etc. Antibodies and compositions comprising antibodies or fragments thereof having such biological activity in vivo and/or in vitro are also provided.

In certain embodiments, an antibody of the invention is tested for such biological activity. See Examples 3-16 for exemplary descriptions of such assays.

D. Immunoconjugates

The invention also provides immunoconjugates comprising an anti-hemagglutinin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

E. Methods and Compositions for Diagnostics and Detection

In certain embodiments, any of the anti-hemagglutinin antibodies provided herein is useful for detecting the presence of hemagglutinin or influenza B virus in a biological sample. The term “detecting” as used herein encompasses quantitative or qualitative detection. In certain embodiments, a biological sample comprises a cell or tissue, such as, for example, lung, upper respiratory tract, nasal canal, blood, sputum, or comprises a biological sample obtained by nasal or throat swab.

In one embodiment, an anti-hemagglutinin antibody for use in a method of diagnosis or detection is provided. In a further aspect, a method of detecting the presence of hemagglutinin or influenza B virus in a biological sample is provided. In certain embodiments, the method comprises contacting the biological sample with an anti-hemagglutinin antibody as described herein under conditions permissive for binding of the anti-hemagglutinin antibody to hemagglutinin, and detecting whether a complex is formed between the anti-hemagglutinin antibody and hemagglutinin. Such method may be an in vitro or in vivo method. In one embodiment, an anti-hemagglutinin antibody is used to select subjects eligible for therapy with an anti-hemagglutinin antibody, e.g., where hemagglutinin is a biomarker for selection of patients.

Exemplary disorders that may be diagnosed using an antibody of the invention include influenza A virus infection, including influenza B virus infection in children, infants, adults, and the elderly.

In certain embodiments, labeled anti-hemagglutinin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-hemagglutinin antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Application Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a neuraminidase inhibitor, an anti-hemagglutinin antibody, an anti-M2 antibody, etc. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-hemagglutinin antibodies provided herein may be used in therapeutic methods.

In one aspect, an anti-hemagglutinin antibody for use as a medicament is provided. In further aspects, an anti-hemagglutinin antibody for use in treating, preventing, or inhibiting influenza B virus infection is provided. In certain embodiments, an anti-hemagglutinin antibody for use in a method of treatment is provided. In certain embodiments, the invention provides an anti-hemagglutinin antibody for use in a method of treating an individual having influenza B virus infection comprising administering to the individual an effective amount of the anti-hemagglutinin antibody. In one such embodiment, the method further comprises administering to the individual an effective amount of at least one additional therapeutic agent, e.g., as described below. In further embodiments, the invention provides an anti-hemagglutinin antibody for use in preventing, inhibiting, or reducing hemagglutinin-mediated fusion between influenza B virus viral membrane and infected cell endosomal membranes, thus preventing viral RNA entry into the infected cell cytoplasm and preventing further propagation of infection. In certain embodiments, the invention provides an anti-hemagglutinin antibody for use in a method of preventing, inhibiting, or treating influenza B virus infection in an individual comprising administering to the individual an effective amount of the anti-hemagglutinin antibody to prevent, inhibit, or treat influenza B virus infection. An "individual" according to any of the above embodiments is preferably a human.

In a further aspect, the invention provides for the use of an anti-hemagglutinin antibody in the manufacture or preparation of a medicament. In one embodiment, the medicament is for treatment of influenza B virus infection. In a further embodiment, the medicament is for use in a method of treating influenza B virus infection comprising administering to an individual having influenza B virus infection an effective amount of the medicament. In one such embodiment, the method further comprises administering to the individual an effective amount of at least one additional therapeutic agent, e.g., as described below. In a further embodiment, the medicament is for preventing, inhibiting, or reducing hemagglutinin-mediated fusion between influenza B virus viral membrane and infected cell endosomal membranes, thus preventing viral RNA entry into the infected cell cytoplasm and preventing further propagation of infection. In a further embodiment, the medicament is for use in a method of preventing, inhibiting, or treating influenza B virus infection in an individual comprising administering to the individual an amount effective of the medicament to prevent, inhibit, or reduce, influenza B virus infection. An "individual" according to any of the above embodiments may be a human.

In a further aspect, the invention provides a method for treating influenza B virus infection. In one embodiment, the method comprises administering to an individual having such influenza B virus infection an effective amount of an anti-hemagglutinin antibody. In one such embodiment, the method further comprises administering to the individual an effective amount of at least one additional therapeutic agent, as described herein. An "individual" according to any of the above embodiments may be a human.

The present invention provides anti-hemagglutinin antibodies effective at inhibiting, preventing, or treating influenza B virus infection in an individual (e.g., a subject or a patient). In some aspects, an anti-hemagglutinin antibody of the present invention is effective at prophylactically treating an individual in order to prevent influenza B virus infection of the individual.

In some aspects, an individual suitable for treatment with an anti-hemagglutinin antibody of the present invention is an individual having or suspected having influenza B virus infection. In some embodiments, such individuals include infants, children, adults, and the elderly. In some embodiments, the individual is hospitalized with influenza B virus infection. In other embodiments, the individual having influenza B virus infection has one or more co-morbidities, such as, for example, immunodeficiency, pregnancy, lung disease, heart disease, renal disease, or co-infection (e.g., a bacterial infection or a viral infection, such as bacterial or viral pneumonia).

In some aspects, treatment of an individual with an anti-hemagglutinin antibody of the present invention reduces influenza B virus infection severity, reduces the length of influenza B virus infection, or reduces influenza B virus infectivity. In other aspects, treatment of influenza B virus infection with an anti-hemagglutinin antibody of the present invention provides additional benefit, including a reduction in the length of hospital stay, reduction or prevention of the need for intensive care unit (ICU) use, reduction or prevention of the need for assisted or mechanical ventilation, reduction or prevention of the need for supplemental oxygen use, and reduction of mortality. In some aspects, the reduction in the length of hospital stay is 1 day, 2 days, 3 days, 4 days, 5 days, or longer than 5 days. In some aspects, the reduction in the need for intensive care unit use is 1 day, 2 days, 3 days, 4 days, 5 days, or longer than 5 days. In some aspects, the reduction in need for assisted or mechanical ventilation is 1 day, 2 days, 3 days, 4 days, 5 days, or longer than 5 days. In some aspects, the reduction in the need for supplemental oxygen is 1 day, 2 days, 3 days, 4 days, 5 days, or longer than 5 days. In some aspects, treatment of an individual with an anti-hemagglutinin antibody of the present invention reduces influenza B virus infection disease symptoms, such as, for example, fever, coryza, chills, sore throat, muscle pain, body aches, headache, cough, nasal congestion, weakness or fatigue, irritated or watering eyes, and general discomfort.

In some aspects, treatment of an individual with an anti-hemagglutinin antibody of the present invention reduces the time to normalization of respiratory function, such as a reduction of time to normalization of respiratory rate, or a reduction of time to normalization of oxygen saturation. In some aspects, treatment of an individual with an anti-hemagglutinin antibody of the present invention reduces the time to return to normal oxygen saturation, e.g., to an oxygen saturation of about 92% or greater, as measured over a 24 hour period without supplemental oxygen administration. In other aspects, treatment of an individual with an anti-hemagglutinin antibody of the present invention reduces the time to normalization of vital signs, such as heart rate, blood pressure, respiratory rate, and temperature.

In some aspects, treatment of an individual with an anti-hemagglutinin antibody of the present invention improves virologic endpoints, such as, for example, influenza virus titer. Virus titer can be measured by various ways known to one of skill in the art, such as, for example, viral area under the curve (AUC), as measured by, for example, qPCR or tissue culture infective dose (TCID50). In some aspects, the treatment results in greater than or equal to 50% reduction in viral AUC as measured by qPCR or TCID50.

In various aspects of the present invention, an anti-hemagglutinin antibody provided herein is effective at treating influenza B virus infection when administered at about 12 hours, at about 24 hours, at about 36 hours, at about 48 hours, at about 60 hours, at about 72 hours, at about 84 hours, and at about 96 hours after onset of symptoms (e.g., onset of illness). In other aspects, an anti-hemagglutinin antibody provided herein is effective at treating influenza B virus infection when administered between about 24 hours and 48 hours after onset of symptoms (e.g., the individual has been symptomatic for between 24 and 48 hours), when administered between about 48 hours and 72 hours after onset of symptoms, or when administered between about 72 hours and 96 hours after onset of symptoms. In certain embodiments of the present invention, an anti-hemagglutinin antibody of the present invention is effective at treating or reducing influenza B virus infection and extends the treatment window of current standard of care (e.g., oseltamivir) beyond 48 hours after onset of symptoms.

In a further aspect, the invention provides pharmaceutical formulations comprising any of the anti-hemagglutinin antibodies provided herein, e.g., for use in any of the above therapeutic methods. In one embodiment, a pharmaceutical formulation comprises any of the anti-hemagglutinin antibodies provided herein and a pharmaceutically acceptable carrier. In another embodiment, a pharmaceutical formulation comprises any of the anti-hemagglutinin antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a neuraminidase inhibitor (e.g., zanamivir, oseltamivir phosphate, amantadine, rimantadine), an anti-M2 antibody, an anti-hemagglutinin antibody, etc. In some aspects, treatment of an individual having influenza B virus infection with an anti-hemagglutinin antibody of the present invention co-administered with a neuraminidase inhibitor provides a synergistic therapeutic effect compared to treatment with either agent alone.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-hemagglutinin antibody and administration of an additional therapeutic agent occur within about one month, or within about one, two, or three weeks, within about one, two, three, four, five, or six days, or within about one, two, three, four, five, six, eight, ten, twelve, sixteen, twenty, or twenty-four hours of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to about 45 mg/kg (e.g., about 1.0 mg/kg to about 15 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Exemplary dosages of the antibody would be in the range from about 1.0 mg/kg to about 45 mg/kg, from about 1.0 mg/kg to about 30 mg/kg, from about 1.0 mg/kg to about 15 mg/kg, from about 1.0 mg/kg to about 10 mg/kg, or from about 1.0 mg/kg to about 5 mg/kg. Thus, one or more doses of about 1.0 mg/kg, 2.5 mg/kg, 5.0 mg/kg, 10 mg/kg, 15 mg/kg, 30 mg/kg, or 45 mg/kg (or any combination thereof) may be administered to the patient. Such doses may be administered intermittently, e.g., every day, every two days, every three days, etc. An initial higher loading dose, followed by one or more lower doses may be administered. Dosing can also be at a fixed dose, such as, for example, 200 mg, 400 mg, 600 mg, 800 mg, 1000 mg, 1200 mg, 1400 mg, 1500 mg, 1600 mg, 1800 mg, 2000 mg, 2200 mg, 2400 mg, 2500 mg, 2600 mg, 2800 mg, 3000 mg, 3200 mg, 3400 mg, 3600 mg, etc. The progress of this therapy is easily monitored by conventional techniques and assays.

It is understood that any of the above formulations or therapeutic methods may be carried out using an immunoconjugate of the invention in place of or in addition to an anti-hemagglutinin antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-hemagglutinin antibody.

III. Examples

The following are examples of methods and compositions of the invention. It is understood that various other embodiments may be practiced, given the general description provided above.

Example 1. Plasmablast Enrichment and Expansion

To discover and identify rare antibodies against influenza B virus hemagglutinin, the following plasmablast enrichment and expansion technique was developed. (See copending patent application U.S. patent application Ser. No. 14/077,414 and International patent application number PCT/US2013/69567, both filed 12 Nov. 2013, and Nakamura et al. (2013) Cell Host & Microbe, 14:93-103, each of which is incorporated by reference herein in its entirety.)

Leukopacs from normal human donors that received the seasonal influenza Fluvirin® vaccine (Novartis Lot #111796P1) 7 days prior to their blood donation were obtained from Blood Centers of the Pacific (San Francisco, Calif.). Peripheral blood mononuclear cells (PBMCs) were isolated from the leukopacs using standard methodologies. Six- to eight-week old female SCID/beige mice were purchased from Charles River Laboratories (Hollister, Calif.) and housed and maintained at Genentech in accordance with American Association of Laboratory Animal Care guidelines. All experimental studies were conducted under the approval of the Institutional Animal Care and Use Committees of Genentech Lab Animal Research in an AAALACi-accredited facility in accordance with the Guide for the Care and Use of Laboratory Animals and applicable laws and regulations. Leukopac or blood from healthy human donors was obtained after written informed consent was provided and ethical approval granted from the Western Institutional Review Board.

In vivo antigen-driven plasmablast enrichment and expansion was performed using intraspenic transplantation of PBMCs as follows. Isolated PBMCs were resuspended with hemagglutinin antigens (see below) (0.1-2 µg antigen for each one million B cells) and incubated for 30 minutes at 37° C. (PBMC/antigen pre-mix). Following this incubation, the PBMCs were washed to remove unbound antigens. To enrich for plasmablasts that produced cross-reactive hemagglutinin antibodies specific to influenza B virus, the hemagglutinin antigen variants used for PBMC/antigen pre-mix and single cell sorting were specifically chosen to differ from the hemagglutinin antigen variants contained within the influenza Fluvirin® vaccine. Hemagglutinin antigens used in this study, therefore, included hemagglutinin from influenza B virus isolates: B/HongKong/1973 (used in antigen-pre-mix and FACS); B/Maryland/1/1959 and B/Wisconsin/2010 (used in ELISA screen); and B/Brisbane/2008 (in vaccine and used in ELISA screen). The hemagglutinin antigens were produced at Genentech using standard molecular biology techniques.

6-8 week old female SCID/beige mice (Charles River Laboratories, Hollister, Calif.) were sub-lethally irradiated with 350 rads using a Cesium-137 source. Polymyxin B (110 mg/L) and neomycin (1.1 g/L) were added to the drinking water for 7 days following irradiation. Four hours after irradiation, the left flank of each mouse was shaved and prepped with Betadine® (Purdue Pharma, Stamford, Conn.) and 70% alcohol. Surgical procedures were performed under anesthesia using aseptic surgical procedures. A 1-cm skin incision was made just below the costal border of each mouse, followed by an incision of the abdominal wall and the peritoneum. The spleen of each mouse was carefully exposed and injected with $50 \times 10^6$ human PBMCs resuspened in 30 μL PBS. The incisions were closed in the muscular layer and in the skin using 5-0 Vicryl® sutures (Ethicon, Somerville, N.J.) and surgical staples, respectively. For antigen-specific cell sorting experiments, mice were sacrificed at 8 days post-transplantation, and their spleens harvested.

Single cell suspensions of spleen cells obtained from the mice were stained with a cocktail of anti-human monoclonal antibodies CD38 PECy7 (BD Biosciences, San Jose, Calif.) and IgG Dylight (Jackson ImmunoResearch Laboratories, Inc., West Grove, Pa.) which define human IgG+ plasmablasts as $CD38^{high}$/IgG+ expression. To identify influenza B virus hemagglutinin cross-reactive plasmablasts within the suspension of isolated spleen cells, the cells were stained with hemagglutinin from influenza B virus strain B/HongKong/1973, which was previously conjugated with FITC or PE, respectively, using Lightning-Link® labeling kits (Innova Biosciences, Cambridge, UK).

Of approximately 2,018 antigen-specific plasmablasts identified using the methods described above, seven mAbs showed viral neutralization against at least one influenza B virus strain, and three mAbs displayed viral neutralization against all influenza B virus strains tested, including influenza B virus strains from ancestral, Yamagata, and Victoria lineages.

Example 2. IgG Cloning from Single Plasmablasts

Influenza B virus hemagglutinin cross-reactive human plasmablasts (described above) were single-cell sorted, resulting in approximately 2,018 antigen-specific plasmablasts. Single plasmablasts were sorted directly into U-bottom 96-well micro-well plates containing 50 μl RPMI containing 5% Low IgG fetal bovine serum. The plates were centrifuged for 5 minutes at 600×g (Beckman Coulter, Brea, Calif.) and the media was carefully removed by aspiration. The cells were resuspended and washed twice in 90 μl of PBS following the same procedure.

To generate cDNA encoding the variable heavy chains and light chains, each cell was resuspended in 6 μl of Reverse Transcriptase (RT) reaction mixture containing 2 units RNaseout (Invitrogen, Grand Island, N.Y.), 0.5 mM 4dNTP (Perkin Elmer, Waltham, Mass.), 1.5 mM $MgCl_2$, 37.5 mM KCl, 10 mM DTT (dithiothreitol), 0.25% Nonidet P40 (US Biological, Marblehead, Mass.), 0.1 mg/ml bovine serum albumin (Sigma-Aldrich), 25 mM Tris pH 8.3, 0.25 pmol of $IgG_{1-4}$ constant, kappa chain constant, and lambda chain constant region specific oligonucleotides (shown below) and 40 U Superscript III (Invitrogen, Grand Island, N.Y.).

| | | |
|---|---|---|
| $IgG_{1-4}$ constant: | GAAGTAGTCCTTGACCAGGCAG | (SEQ ID NO: 1) |
| Kappa constant: | CTCAGCGTCAGGGTGYTGCTGAG | (SEQ ID NO: 2) |

-continued

| | | |
|---|---|---|
| Lambda constant: | GGGTKTGGTSGTCTCCAC | (SEQ ID NO: 3) |

The reaction was incubated for 3×30-minute intervals at 45° C., 50° C., and 55° C. each. Following the incubation, the reaction mixture was diluted to 15 μl with TE buffer (10 mm Tris HCl, 1 mM EDTA). Initial polymerase chain reactions (PCR) were performed to amplify IgG heavy chains, kappa chains, and lambda chains using 2 μl of the diluted RT cocktail from above and Advantage-GC 2 Polymerase Mix (Clontech, Mountain View, Calif.), following protocols provided by the manufacturers. The PCR amplifications were performed using degenerate oligonucleotides based on variable heavy chain and light chain germline and constant region sequences shown below.

| | | |
|---|---|---|
| IGVH1a | CAGGTGCAGCTGGTGCAGTCTGGGGC | (SEQ ID NO: 4) |
| IGVH1b | CAGGTCCAGCTGGTGCAGTCTGGGGC | (SEQ ID NO: 5) |
| IGVH2 | CAGGTCACCTTGAAGGAGTCTGGTCC | (SEQ ID NO: 6) |
| IGVH3 | GAGGTGCAGCTGGTGGAGTCTGGGGG | (SEQ ID NO: 7) |
| IGVH4 | CAGGTGCAGCTGCAGGAGTCGGGCCC | (SEQ ID NO: 8) |
| IGVH5 | GAGGTGCAGCTGGTGCAGTCTGG | (SEQ ID NO: 9) |
| IGVH6 | CAGGTACAGCTGCAGCAGTCAGGTCC | (SEQ ID NO: 10) |
| IGVH7 | CAGGTGCAGCTGGTGCAATCTGG | (SEQ ID NO: 11) |
| IGKV1 | GHCATCCRGWTGACCCAGTCTC | (SEQ ID NO: 12) |
| IGKV2 | GATRTTGTGATGACYCAGWCTC | (SEQ ID NO: 13) |
| IGKV3 | GAAATWGTRWTGACRCAGTCTC | (SEQ ID NO: 14) |
| IGKV4 | GACATCGTGATGACCCAGTCTCC | (SEQ ID NO: 15) |
| IGKV5 | GAAACGACACTCACGCAGTCTC | (SEQ ID NO: 16) |
| IGKV6 | GAWRTTGTGMTGACWCAGTCTC | (SEQ ID NO: 17) |
| IGLV1 | CAGTCTGTGYTGACKCAGCCRCCCTC | (SEQ ID NO: 18) |
| IGLV2 | CAGTCTGCCCTGACTCAGCCT | (SEQ ID NO: 19) |
| IGLV3 | TCCTATGAGCTGACWCAGSHVCCCKC | (SEQ ID NO: 20) |
| IGLV4 | CAGCCTGTGCTGACTCARTCVCCCTC | (SEQ ID NO: 21) |
| IGLV5 | CAGCCTGTGCTGACTCAGCCAACTTC | (SEQ ID NO: 22) |
| IGLV6 | AATTTTATGCTGACTCAGCCCCAC | (SEQ ID NO: 23) |

```
                                      (SEQ ID NO: 24)
IGLV7            CAGGCTGTGGTGACTCAGGAGCCC (SEQ ID NO: 25)
IGLV8            CAGACTGTGGTGACCCAGGAGCC (SEQ ID NO: 26)
IGLV9            CAGCCTGTGCTGACTCAGCCACC (SEQ ID NO: 27)
HC301.5constant  GCAGCCCAGGGCSGCTGTGC (SEQ ID NO: 28)
Kappa102constant GCACACAACAGAGGCAGTTCCAG (SEQ ID NO: 29)
Lambda202constant CTTGRAGCTCCTCAGAGGAG
```

Heavy chain and light chain PCR amplification reactions were each divided into two reactions as follows: heavy chain families VH.1,2,3 (primers IGVH1a, IGVH1b, IGVH2, IGVH3) and VH.4,5,6,7 (primers IGVH4, IGVH5, IGVH6, and IGVH7); kappa chain families VK.1,2,3 (primers IGKV1, IGKV2, and IGKV3) and VK.4,5,6 (primers IGVK4, IGVK5, and IGVK6); and lambda chain families VL.1,2,3,4,5 (IGLV1, IGLV2, IGLV3, IGLV4, and IGLV5) and VL.6,7,8,9 (primers IGLV6, IGLV7, IGLV8, and IGLV9). A touchdown PCR amplification protocol was used for temperature cycling.

Following the reaction, PCR amplification products were treated with Exonucleasel (Exo) and Shrimp Alkaline Phosphatase (SAP) to remove excess nucleotides and primers from each of the PCR amplification reactions (U.S. Biologicals, Marblehead, Mass.). Initial PCR amplification products were directly sequenced to determine the variable sequences of both the heavy chains and light chains using Sanger sequencing. Second nested PCR amplifications were performed using germline-matched heavy chain and light chain variable oligonucleotides in order to insert a mammalian signal and constant region cloning sequences using the following oligonucleotide primers.

```
sVH1a:
                                                (SEQ ID NO: 30)
CCACCATGGGATGGTCATGTATCATCCTTTTTCTAGTAGCAACTGCAACT
GGAGTACATTCACAGGTGCAGCTGGTGCAGTCTGGGGCTGAGGTGAAG sVH2:
                                                (SEQ ID NO: 31)
CCACCATGGGATGGTCATGTATCATCCTTTTTCTAGTAGCAACTGCAACT
GGAGTACATTCACAGATCACCTTGAAGGAGTCTGGTCCTACGCTGGTG sVH3vv:
                                                (SEQ ID NO: 32)
CCACCATGGGATGGTCATGTATCATCCTTTTTCTAGTAGCAACTGCAACT
GGAGTACATTCACAGGTGCAGCTGGTGGAGTCTGGGGGAGGCGTGGTC sVH3g1:
                                                (SEQ ID NO: 33)
CCACCATGGGATGGTCATGTATCATCCTTTTTCTAGTAGCAACTGCAACT
GGAGTACATTCAGAGGTGCAGCTGGTGGAGTCTGGGGAGGCTTG sVH4:
                                                (SEQ ID NO: 34)
CCACCATGGGATGGTCATGTATCATCCTTTTTCTAGTAGCAACTGCAACT
GGAGTACATTCACAGGTGCAGCTGCAGGAGTCGGGCCCAGGACTGG sVH5:
                                                (SEQ ID NO: 35)
CCACCATGGGATGGTCATGTATCATCCTTTTTCTAGTAGCAACTGCAACT
GGAGTACATTCAGAGGTGCAGCTGGTGCAGTCTGGAGCAGAGGTGAAAAA
G sVH6:
                                                (SEQ ID NO: 36)
CCACCATGGGATGGTCATGTATCATCCTTTTTCTAGTAGCAACTGCAACT
GGAGTACATTCACAGGTACAGCTGCAGCAGTCAGGTCCAGGACT sVH7:
                                                (SEQ ID NO: 37)
CCACCATGGGATGGTCATGTATCATCCTTTTTCTAGTAGCAACTGCAACT
GGAGTACATTCACAGGTGCAGCTGGTGCAATCTGGGTCTGAGTTG sVK1:
                                                (SEQ ID NO: 38)
CCACCATGGGATGGTCATGTATCATCCTTTTTCTAGTAGCAACTGCAACT
GGAGTACATTCAGACATCCAGATGACCCAGTCTCCATCCTCCCTG sVK2:
                                                (SEQ ID NO: 39)
CCACCATGGGATGGTCATGTATCATCCTTTTTCTAGTAGCAACTGCAACT
GGAGTACATTCAGATATTGTGATGACTCAGTCTCACTCTCCCTGC sVK3:
                                                (SEQ ID NO: 40)
CCACCATGGGATGGTCATGTATCATCCTTTTTCTAGTAGCAACTGCAACT
GGAGTACATTCAGAAATTGTGTTGACACAGTCTCCAGCCACCCTGTCTTT
G sVK4:
                                                (SEQ ID NO: 41)
CCACCATGGGATGGTCATGTATCATCCTTTTTCTAGTAGCAACTGCAACT
GGAGTACATTCAGACATCGTGATGACCCAGTCTCCAGACTCCCTGGCTGT
G sVK5:
                                                (SEQ ID NO: 42)
CCACCATGGGATGGTCATGTATCATCCTTTTTCTAGTAGCAACTGCAACT
GGAGTACATTCAGAAACGACACTCACGCAGTCTCCAGC sVK6:
                                                (SEQ ID NO: 43)
CCACCATGGGATGGTCATGTATCATCCTTTTTCTAGTAGCAACTGCAACT
GGAGTACATTCAGAAATTGTGCTGACTCAGTCTCCAGACTTTCG sVL1:
                                                (SEQ ID NO: 44)
CCACCATGGGATGGTCATGTATCATCCTTTTTCTAGTAGCAACTGCAACT
GGAGTACATTCACAGTCTGTGYTGACKCAGCCRCCCTC sVL2:
                                                (SEQ ID NO: 45)
CCACCATGGGATGGTCATGTATCATCCTTTTTCTAGTAGCAACTGCAACT
GGAGTACATTCACAGTCTGCCCTGACTCAGCCT sVL3:
                                                (SEQ ID NO: 46)
CCACCATGGGATGGTCATGTATCATCCTTTTTCTAGTAGCAACTGCAACT
GGAGTACATTCATCCTATGAGCTGACWCAGSHVCCCKC
```

-continued sVL4:
(SEQ ID NO: 47)
CCACCATGGGATGGTCATGTATCATCCTTTTTCTAGTAGCAACTGCAACT

GGAGTACATTCACAGCCTGTGCTGACTCARTCVCCCTC sVL5:
(SEQ ID NO: 48)
CCACCATGGGATGGTCATGTATCATCCTTTTTCTAGTAGCAACTGCAACT

GGAGTACATTCACAGCCTGTGCTGACTCAGCCAACTTC sVL6:
(SEQ ID NO: 49)
CCACCATGGGATGGTCATGTATCATCCTTTTTCTAGTAGCAACTGCAACT

GGAGTACATTCAAATTTTATGCTGACTCAGCCCCAC sVL7:
(SEQ ID NO: 50)
CCACCATGGGATGGTCATGTATCATCCTTTTTCTAGTAGCAACTGCAACT

GGAGTACATTCACAGGCTGTGGTGACTCAGGAGCCC sVL8:
(SEQ ID NO: 51)
CCACCATGGGATGGTCATGTATCATCCTTTTTCTAGTAGCAACTGCAACT

GGAGTACATTCACAGACTGTGGTGACCCAGGAGCC wVL9:
(SEQ ID NO: 52)
CCACCATGGGATGGTCATGTATCATCCTTTTTCTAGTAGCAACTGCAACT

GGAGTACATTCACAGCCTGTGCTGACTCAGCCACC

Heavy constant:
(SEQ ID NO: 53)
GCCAGGGGGAAGACCGATG

Kappa constant:
(SEQ ID NO: 54)
CTGGGATAGAAGTTATTCAGCAGGCACACAACAGAAGCAGTTCCAGATTT

CAACTGCTC

Lambda constant:
(SEQ ID NO: 29)
CTTGRAGCTCCTCAGAGGAG

PCR amplification reactions were set up using PrimeStar HS DNA Polymerase with GC (Takara Bio, Shiga, Japan) according to the manufacturer's recommendation. Following the PCR amplification reactions, the amplification products were treated with Exo/SAP as described above. Heavy variable chain and light variable chain encoding PCR amplification products were inserted into a mammalian expression vector using restriction endonuclease free procedures. 20 µl of the PCR amplification products were annealed onto single stranded DNA human templates for IgG$_1$, kappa, and lambda chain using the Kunkel mutagenesis protocol. (See Kunkel (1985) PNAS 82:488-492.) Correctly inserted constructs were confirmed by DNA sequencing. Plasmids containing nucleic acids encoding heavy chains and light chains were co-transfected into 293T human embryonic kidney cells using Fugene transfection reagent (Roche Diagnostic, Indianapolis, Ind.) for transient expression, and analyzed for expression and binding as described below.

Example 3. Hemagglutinin ELISA Screening Assay

The ability of each monoclonal anti-hemagglutinin antibody (i.e., anti-influenza B virus antibody) obtained as described above to bind various hemagglutinin subtypes from different influenza B virus isolates was examined by ELISA as follows. Various hemagglutinin-expressing plasmids were transfected into 293T cells; these included hemagglutinin from influenza B virus strains B/Maryland/1/1959, B/Victoria/2000, and B/Brisbane/2008. After two days, cells were lysed in 50 mM Tris, pH 8, 5 mM EDTA, 150 mM NaCl, 1% Triton X-100 plus protease inhibitor cocktail (Roche). Nuclei were cleared by centrifugation and the resulting lysates were stored at −80° C.

For ELISA screening, 384-well plates (Nunc MaxiSorp) were coated with 5 µg/ml *Galanthus nivalis* lectin (Sigma) in PBS. The plates were washed and then coated with dilutions of the cell lysates containing various expressed hemagglutinins. The plates were washed and incubated with various dilutions of the anti-hemagglutinin antibodies and subsequently with a goat-anti-human-HRP secondary antibody (Jackson). Plates were washed and processed for TMB (3,3',5,5'-tetramethylbenzidine) substrate detection.

Approximately 2,018 plasmablasts were obtained from single-cell sorting described above in Example 2. Of this, 98 monoclonal antibodies transiently expressed in 293T cells and screened by ELISA displated binding to hemagglutinin from influenza B virus strains B/Maryland/1/1959, B/Victoria/2000, and B/Brisbane/2008.

Example 4. In Vitro Influenza B Virus Neutralization

The ability of the anti-influenza B virus hemagglutinin antibodies of the present invention to elicit broad hemagglutinin subtype binding and neutralization of a panel of influenza B virus isolates in vitro was examined as follows. MDCK cells were grown in DMEM media supplemented with 10% FBS as a 25% confluent monolayer in 96-well black-wall with clear-bottom imaging plates (Costar 3904). Each Influenza B virus subtype was diluted in influenza media (DMEM, 0.2% BSA from Gibco Cat#15260, 10 mM HEPES, Penicillin/Streptomycin/Glutamin from Gibco Cat#10378, 2 ug/mL TPCK treated Trypsin from Sigma Cat# T1426) to an MOI of 1 and incubated for 1 hour at 37° C. with varying concentrations of mAb 34B5A and mAb 33F8 ranging from 0.02 to 1,600 nM. Each antibody/influenza virus cocktail was then allowed to infect the MDCK cells for 16 hours at 37° C. in a 5% CO$_2$ incubator prior to fixation of the cells with cold 100% ethanol. The fixed cells were then stained with Hoechst 33342 (Invitrogen Cat# H3570) to visualize cell nuclei and determine total cell number. The cells were also stained sequentially with a broadly reactive monoclonal antibody (Millipore Cat# MAB8258) specific for the influenza B virus nucleoprotein (NP) and an Alexa Fluor 488-conjugated goat anti-mouse secondary antibody (Invitrogen Cat# A11029) to determine the number of infected cells. Cells were imaged using an Image Express Micro instrument (Molecular Devices) and data images were analyzed using MetaXpress 3.1 software.

The percentage of infected cells was determined and plotted on the Y-axis versus the antibody concentration (Log$_{10}$) on the X-axis. All neutralization assays were completed in triplicate and data is reported as IC50 values in nM with 95% confidence intervals (95% CI). The data were fit with a nonlinear regression dose response curve to generate the IC50 and 95% CI.

Figure 1B:
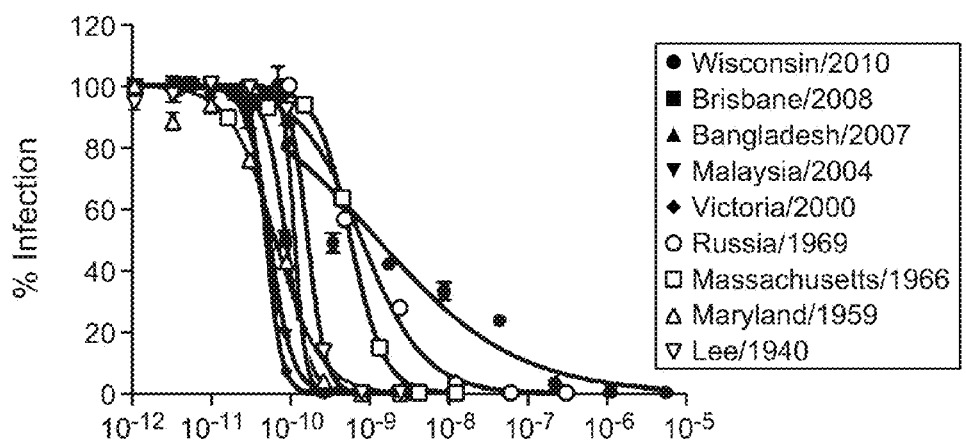

In vitro neutralization dose-response curves were generated using various concentrations of the monoclonal antibodies described herein against a broad panel of influenza B virus strains. FIGS. 1A and 1B show neutralization curves of mAb 34B5A and mAb 33F8 against a panel of influenza B virus strains, respectively. As shown in FIGS. 1A and 1B, mAb 34B5A and mAb 33F8 were effective at in vitro neutralization of a broad panel of influenza B virus strains, including in vitro neutralization activity against ancestral influenza B virus lineages, as well as influenza B viruses from Yamagata and Victoria lineages.

Table 2 below shows in vitro neutralization activity calculations from the experiments described above for mAb 34B5A.

TABLE 2

| Influenza B Virus Strain | Lineage | IC50 (nM) | 95% CI (nM) |
|---|---|---|---|
| B/Wisconsin/1/2010 | Yamagata | 2.9 | 1.3-6.4 |
| B/Brisbane/2008 | Victoria | 0.054 | 0.047-0.063 |
| B/Bangladesh/2007 | Victoria | 0.19 | 0.17-0.21 |
| B/Malaysia/2004 | Victoria | 0.038 | 0.024-0.059 |
| BNictoria/504/2000 | Yamagata | 0.092 | 0.088-0.096 |
| B/Russia/1969 | Ancestral | 0.79 | 0.61-1.0 |
| B/Massachusettes/3/1966 | Ancestral | 0.38 | 0.33-0.44 |
| B/Maryland/1/1959 | Ancestral | 0.038 | 0.029-0.050 |
| B/Lee/10/1940 | Ancestral | 0.14 | 0.13-0.15 |

Figure 2:
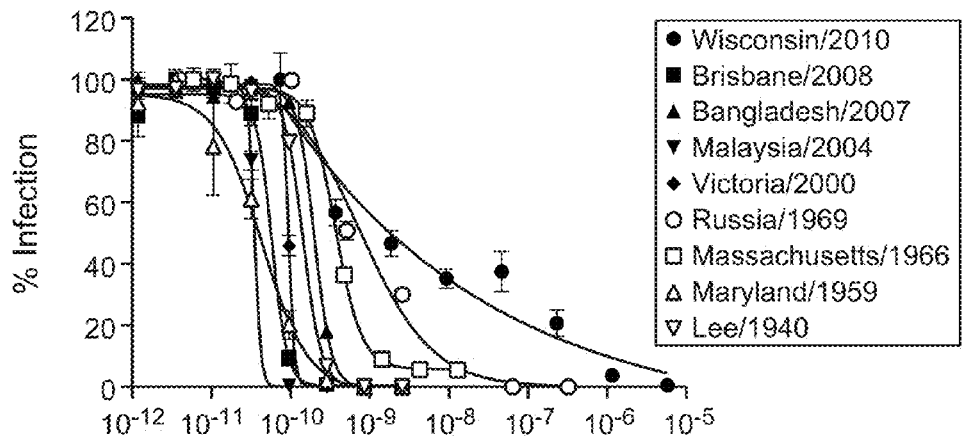
FIG. 2 sets forth data showing in vitro neutralization of various influenza B virus isolates by monoclonal antibody 46B8A.

FIG. 2 shows in vitro neutralization curves of mAb 46B8A against a panel of influenza B virus strains. Additionally, as shown in FIG. 2, mAb 46B8A was effective at in vitro neutralization of a broad panel of influenza B virus strains, including in vitro neutralization activity against ancestral influenza B virus lineages, as well as influenza B viruses from Yamagata and Victoria lineages.

These results showed that monoclonal antibodies of the present invention were able to neutralize in a dose-dependent manner various influenza B virus isolates/strains in vitro. Additionally, these results showed that monoclonal antibodies of the present invention were able to neutralize ancestral influenza B virus isolates as well as influenza B virus isolates from post-divergence of Yamagata and Victoria lineages, including neutralization of influenza B virus strains Wisconsin/2010, Brisbane/2008, Bangladesh/2007, Malaysia/2004, Victoria/2000, Russia/1969, Massachusetts/1966, Maryland/1959, and Lee/1940.

These results indicated that monoclonal antibodies of the present invention are effective in the treatment and prevention of influenza B virus infection and influenza B virus strains from ancestral, Yamagata, and Victoria lineages.

Example 5. Influenza B Virus Hemagglutination Inhibition Assay

To examine the mechanism of neutralization by mAb 46B8C and mAb 34B5C, hemagglutination inhibition (HI) assays were performed using two influenza B viruses: B/Victoria/504/2000 and B/Wisconsin/1/2010. For each influenza B virus, eight serial dilutions in 5-fold steps were made in duplicate in phosphate buffered saline (PBS), starting at 1:5. Fifty μl of each dilution was transferred into V-bottom 96-well plate (Costar 3894). Turkey red blood cells (TRBCs, from Lampire Biological Laboratories Cat#7249408) were diluted to 0.5% in PBS and 50 μl was added to each well containing virus. The plate was incubated at room temperature for 1 hour. The last virus dilution (corresponding to the lowest virus concentration) that prevented TRBC aggregation was determined by direct visualization and used for hemagglutination inhibition (HI) assay.

HI assay was performed with mAb 46B8C and mAb 34B5C, two human monoclonal antibodies (huMab) with broad influenza B virus hemagglutinin subtype binding, and a control huMab gD5237, which is specific for the glycoprotein D of Herpes Simplex Virus (HSV). Eight serial dilutions of each antibody in 5-fold steps ranging from 0.0032-250 μg/ml (in triplicate) were mixed with pre-determined amount of B/Victoria/504/2000 or B/Wisconsin/1/2010 virus in PBS and incubated at 37° C. for 1 hour, as described above. Fifty μl of the virus-antibody mixture was transferred into V-bottom 96-well plate. TRBCs were diluted to 0.5% in PBS and 50 μl was added to each well containing 50 μl virus-antibody mixtures. Each plate was incubated at room temperature for 1 hour and HI titers (i.e., lowest antibody concentration effective at inhibition of hemagglutination) were determined for each antibody by direct visualization.

Figure 3:
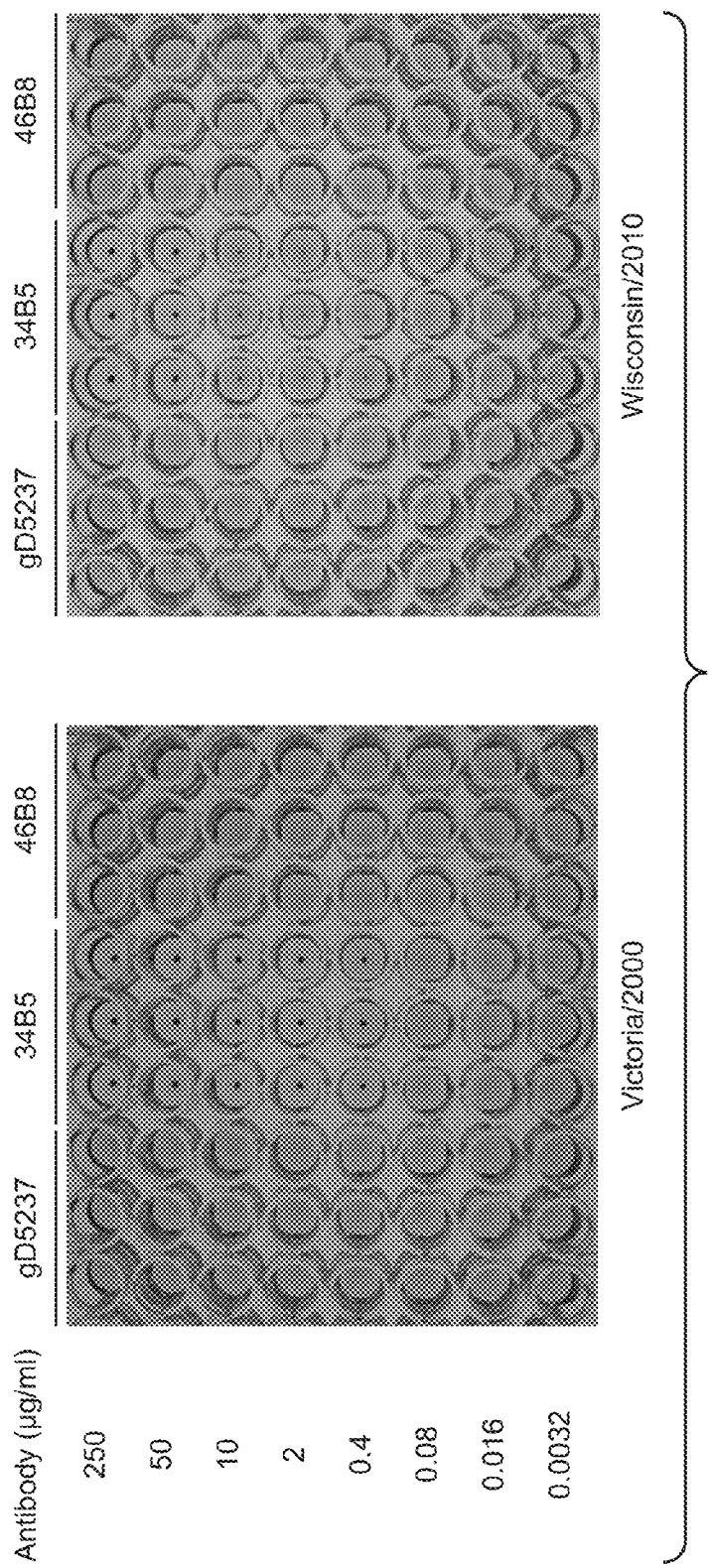
FIG. 3 sets forth data showing the effect of monoclonal antibody 34B5C and monoclonal antibody 46B8C on hemagglutination inhibition.

As shown in FIG. 3, mAb 34B5C was effective at inhibition of hemagglutination of turkey red blood cells (TRBCs) by both B/Victoria/504/2000 and B/Wisconsin/1/2010 influenza B viruses.

In contrast, neither mAb 46B8C nor the control gD5237 antibody showed inhibition of hemagglutination by either influenza B virus, even at the highest antibody concentration tested. These results suggested that mAb 34B5C binds to the receptor-binding domain in the head group of influenza B virus hemagglutinin and thus prevents the binding of the viruses to the sialic acid receptor on TRBC. These results also suggested that mAb 46B8C binds to an area on influenza B virus hemagglutinin that is outside the receptor-binding domain (e.g., the stalk (or stem) region).

Example 6. In Vitro Influenza B Virus Neutralization by Plaque Inhibition Assay

The ability of anti-influenza B virus hemagglutinin antibodies of the present invention to neutralize various influenza B virus isolates was further analyzed as follows. Influenza B virus titer was determined by plague assay as follows. MDCK cells were grown in DMEM media supplemented with 10% FBS as a confluent monolayer in 6-well tissue culture plates (Costar 3516). All influenza B virus strains used in these studies were purchased from ViraPur (Dan Diego, Calif.). For virus titer determination, each virus stock was diluted in influenza media (DMEM, 0.2% BSA from Gibco Cat#15260, 10 mM HEPES, Penicillin/Streptomycin/Glutamin from Gibco Cat#10378, 2 ug/mL TPCK treated trypsin from Sigma Cat# T1426). Six serial dilutions in 10-fold steps were made for each virus, from $1:10^2$ to $1:10^7$, and 1 ml of each was used to infect MDCK cells in 6-well plate. Two hours after infection, virus was removed and cells were overlaid with 2 ml of a 1:1 mixture of 2× influenza media:2% agarose. The plates were kept at room temperature for 30 minutes and then incubated at 37° C. in a 5% $CO_2$ incubator. Three days later, plaques were counted by direct visualization under opaque light, and titer of each virus was determined in plaque forming units (PFU)/ml.

The effect of monoclonal antibodies of the present invention on influenza B virus neutralization by a plaque inhibition assay was then examined as follows. MDCK cells were grown in DMEM media supplemented with 10% FBS as a confluent monolayer in 6-well tissue culture plates (Costar 3516). For each influenza B virus, the amount of virus that resulted in 20 to 200 plaques per well in a 6-well plate (determined as described above) was used in the plaque inhibition assay. Six serial dilutions of mAb 46B8C in 3-fold steps ranging from 0.16 to 38.4 nM were mixed with each virus in influenza media and incubated at 37° C. for 1 hour. One ml of the virus-antibody mixture was used to infect MDCK cells in 6-well plates, and each infection was carried out in 3 triplicate plates. The same serial dilutions of mAb 46B8C were made in 2× influenza media and mixed at 1:1 with 2% agarose. Two hours after infection, virus-antibody mixture was removed and cells were overlaid with 2 ml of the antibody-agarose mixture. The plates were kept at room temperature for 30 minutes and then incubated at 37° C. in a 5% $CO_2$ incubator. Five to six days later, plaques were counted by direct observation under opaque light. The percentage of infection was determined by normalizing to the highest plaque number (at the lowest antibody concentration) and plotted on the Y-axis versus the Log 10 antibody concentration on the X-axis. The data were fit with a nonlinear regression dose response curve to generate the IC50 (concentration that gave 50% inhibition) values with 95% confidence intervals (95% CI).

Figure 4:
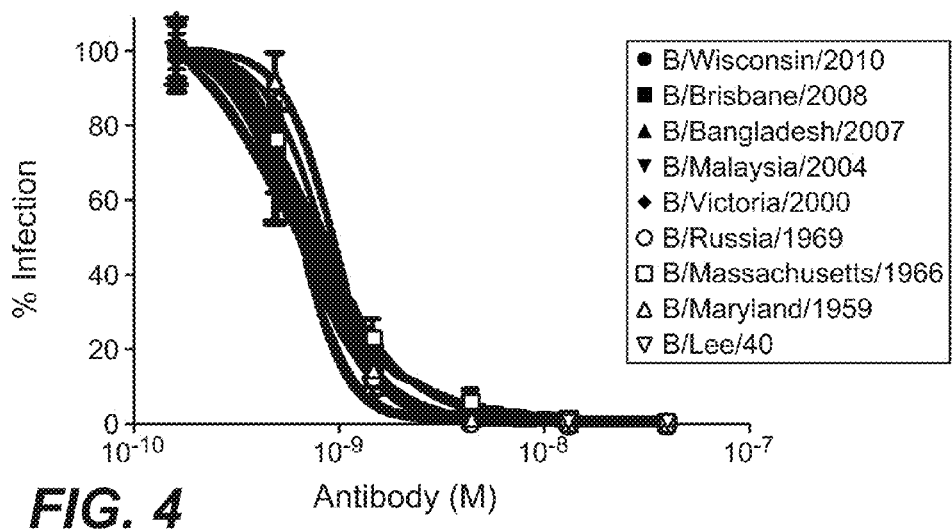
FIG. 4 sets forth data showing neutralization of various influenza B virus isolates by monoclonal antibody 46B8C by in vitro plaque inhibition assay.

As shown in FIG. 4, mAb 46B8C blocked in vitro plaque formation against all influenza B virus strains tested in a dose-dependent manner. IC50 values calculated from the data generated in the plaque formation assay with mAb 46B8C described above is shown in Table 3 below. As seen in Table 3, mAb 46B8C blocked plaque formation at very low concentrations, exhibiting IC50 values less than 1 nM.

TABLE 3

| Influenza Strain | Lineage | IC50 (nM) | 95% CI (nM) |
|---|---|---|---|
| B/Wisconsin/1/2010 | Yamagata | 0.64 | 0.53-0.76 |
| B/Brisbane/2008 | Victoria | 0.86 | 0.72-1.0 |
| B/Bangladesh/2007 | Victoria | 0.75 | 0.62-0.92 |
| B/Malaysia/2004 | Victoria | 0.58 | 0.36-0.91 |
| BNictoria/504/2000 | Yamagata | 0.67 | 0.62-0.73 |
| B/Russia/1969 | Ancestral | 0.73 | 0.61-0.86 |
| B/Massachusettes/3/1966 | Ancestral | 0.80 | 0.65-0.98 |
| B/Maryland/1/1959 | Ancestral | 0.95 | 0.71-1.3 |
| B/Lee/10/1940 | Ancestral | 0.68 | 0.55-0.85 |

Taken together, these data indicated that monoclonal antibodies of the present invention are effective at inhibiting and neutralizing influenza B virus in vitro plaque formation using a plaque neutralization assay, including influenza B virus isolates from ancestral, Yamagata, and Victoria lineages. Additionally, these results showed that monoclonal antibodies of the present invention inhibit influenza B virus in vitro plaque formation at IC50 values below 1 nM.

Example 7. Influenza B Virus Hemagglutinin Fusion Inhibition Assay

To further explore the mechanism of neutralization by mAb 46B8C and mAb 34B5C, the inhibitory effect of these antibodies in a hemagglutinin-mediated cell-cell fusion assay that bypasses the initial receptor binding step during virus entry was examined as follows. HeLa cells were grown in DMEM+10% FBS to ~40% confluent in 6-well tissue culture plates (Costar 3516). Cells in each well were transfected with 10 mg of a plasmid expressing the B/Wisconsin/1/2010 hemagglutinin. Seventeen hours later, transfection mix was removed from the cells and fresh media containing 10 mM sodium butyrate was added to cells. Media was replaced again 6 hours later and cells were allowed to grow overnight to ~80% confluent, after which a fusion inhibition assay was performed.

Cells were washed in PBS and treated with 5 mg/ml TPCK trypsin (Sigma Cat# T1426) in PBS for 7 minutes at 37° C. Trypsin was removed, culture media containing 50 mg/ml soybean trypsin inhibitor (CalBiochem Cat#65035) was added and cells were incubated for 10 minutes at 37° C. Cells were then incubated at 37° C. in culture media containing 20 mg/ml or 200 mg/ml of mAb 46B8C, mAb 34B5C, or control human mAb gD5237, specific for the glycoprotein D of Herpes Simplex Virus (HSV). After 1 hour, antibody was removed and the cells were incubated in influenza media (pH 4.85) for 5 minutes at 37° C. Low-pH media was removed and cells were incubated in growth media overnight at 37° C. to allow full formation of syncytia. Phase images of the cells were taken under 10× objective with a Nikon Eclipse TE2000-E microscope and an NIS-Elements AR3.2 software.

Figure 5:
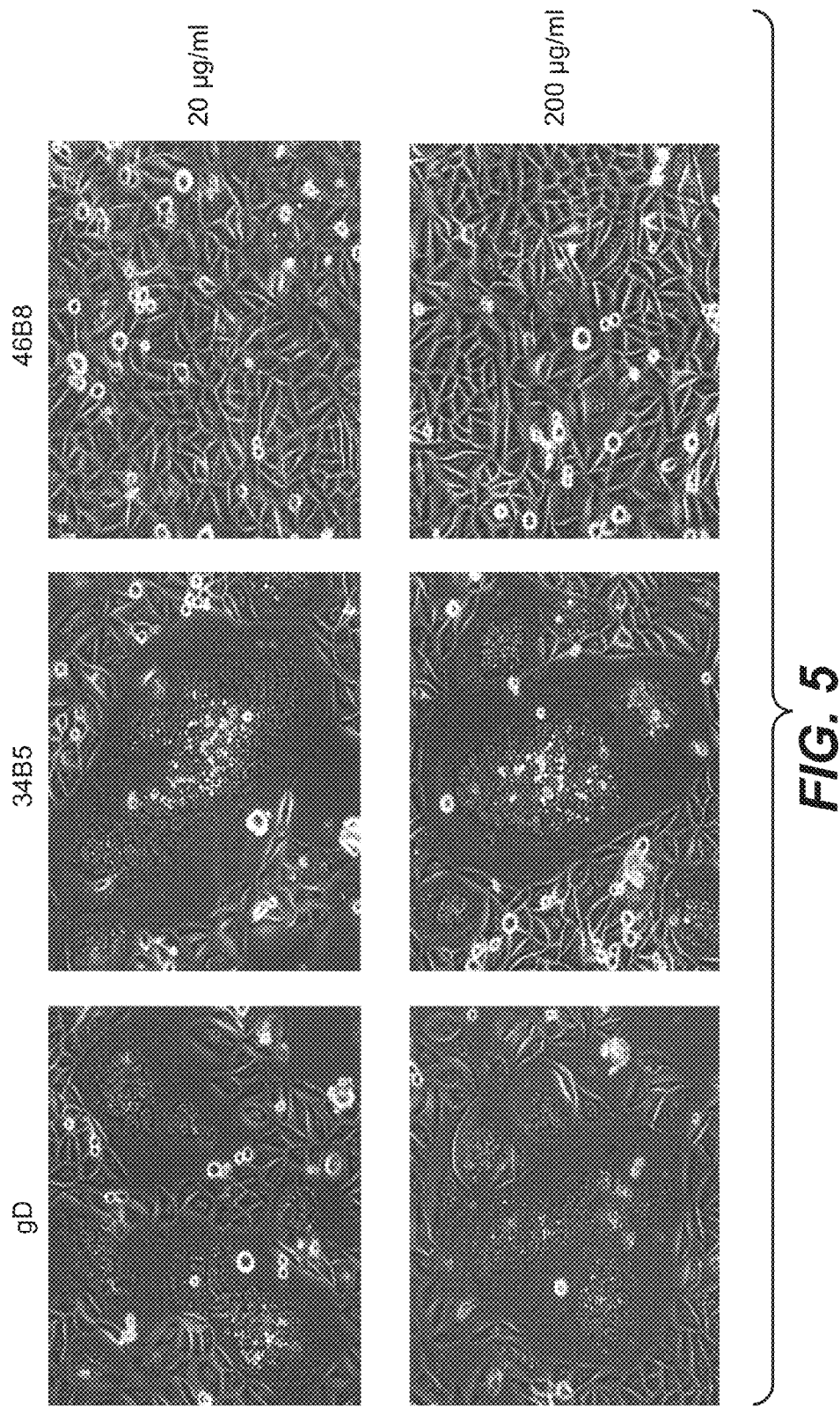
FIG. 5 sets forth data showing the effects of monoclonal antibody 34B5C and monoclonal antibody 46B8C on hemagglutinin-mediated cell-cell fusion.

HeLa cells expressing influenza B virus B/Wisconsin/1/2010 hemagglutinin were incubated with 20 μg/ml or 200 μg/ml of mAb 46B8C, mAb 34B5C, or control mAb gD5237 before exposure to low-pH media. Syncytia appeared within a few hours of the pH drop and fully developed after overnight culture. mAb 46B8C inhibited syncytia formation at both 20 μg/ml and 200 μg/ml; in contrast, neither mAb 34B5C nor control mAb gD5237 blocked cell-cell fusion, at either concentration examined. (See FIG. 5.)

Consistent with the results obtained in the hemagglutination inhibition (HI) assay described above in Example 5, these results suggested that mAb 46B8C is a hemagglutinin stalk-binding antibody and thus able to block the pH-induced conformational change in the hemagglutinin stalk required for influenza B virus membrane fusion. These results also suggested that mAb 34B5C likely binds to the head group of hemagglutinin and neutralizes influenza B virus by blocking the initial receptor binding step, a step which is bypassed in the cell-cell fusion assay described herein.

Example 8. Affinity of mAb 46B8C to Various Influenza B Virus Hemagglutinins

The affinity of mAb46B8 to various influenza B virus hemagglutinins was determined as follows. Competition reaction mixtures of 50 μL containing a fixed concentration of iodinated anti-influenza B virus antibody (mAb 46B8C) and serially diluted concentrations of unlabeled anti-influenza B virus antibody (mAb 46B8C) in binding buffer (DMEM with 2% FBS, 50 mM HEPES, pH 7.2 and 0.1% sodium azide) were placed into 96-well plate. 293 cells transiently expressing influenza B viruses of various strains were added to the competition reaction mixtures at a density of 50,000 cells per 0.2 ml in binding buffer. Competition reactions with cells were incubated for 2 hours at room temperature. After the 2-hour incubation, the competition reactions were transferred to a Millipore Multiscreen filter plate and washed four times with binding buffer to separate the free from bound iodinated antibody. The filters were counted on a Wallac Wizard 1470 gamma counter (PerkinElmer Life and Analytical Sciences; Wellesley, Mass.). The binding data were evaluated using New Ligand software (Genentech), which uses the fitting algorithm of Munson and Rodbard to determine the binding affinity (Munson and Rodbard (1980) Anal Biochem 7:2239).

Table X below shows Scatchard binding analysis of mAb 46B8C to hemagglutinin trimers from various influenza B viruses recombinantly expressed on the surface of 293T cells. As shown in Table 4 below, mAb 46B8C displayed low-nM affinity to various influenza B virus hemagglutinins

TABLE 4

| Influenza B Virus Strain | mAb 46B8C $K_D$, nM (% error) | Antigen Density Sites/Cell |
| --- | --- | --- |
| Massachusetts/1966 | 2.5 (16%) | 776,000 |
| Russia/1969 | 2.9 (10%) | 540,000 |
| Wisconsin/2010 | 4.9 (14%) | 1.98e6 |
| Brisbane/2008 | 5.6 (12%) | 1.40e6 |
| Victoria/2000 | 3.5 (12%) | 331,000 |

Example 9. In Vivo Efficacy of mAb 34B5A in Mice Against B/Victoria/2000 and B/Wisconsin/2010

The in vivo efficacy of mAb 34B5A to influenza B virus infection in mice was performed as follows. DBA/2J mice (Jackson Lab, Bar Harbor, Me.) were infected intra-nasally with 50 µl of influenza B virus strain B/Victoria/2000 diluted in influenza media (DMEM, 0.2% BSA, 2 µg/mL TPCK-treated trypsin) at the minimum $LD_{100}$ dose ($1 \times 10^4$ virus/mouse). Influenza virus infection was allowed to progress for 72 hours (for B/Victoria/2000 infection) prior to the intravenous administration of mAb 34B5A.

After 72 hours post influenza B virus B/Victoria/2000 infection, various amounts of mAb 34B5A were administered intravenously to the mice at a dose of 15 mg/kg, 3 mg/kg, 0.6 mg/kg, and 0.12 mg/kg in 200 µl PBS. Control treated animals were administered mAb gD5237 at the highest tested equivalent dose of mAb 34B5A (i.e., approximately 15 mg/kg). Mice were monitored daily for body conditioning and survival, and also weighed daily, until 21 days after infection.

Figure 6A:
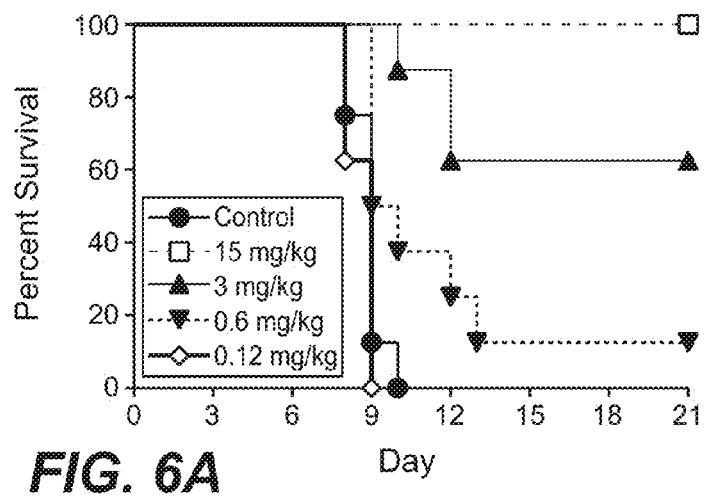
FIGS. 6A and 6B set forth data showing percent survival of mice infected with influenza B virus B/Victoria/2000 and administered various amounts of monoclonal antibody 34B5A (FIG. 6A) compared to that of mice administered TAMIFLU® oseltamivir phosphate (FIG. 6B).

FIG. 6A shows percent survival (over time, in days) of mice administered various amounts of mAb 34B5A 72 hours after infection with influenza B virus B/Victoria/2000. As shown in FIG. 6A, 100% mortality was observed by day 10 in infected mice administered control antibody. However, infected mice administered monoclonal antibody of the present invention showed increased survival. In particular, 100% survival was observed in mice infected with influenza B virus B/Victoria/2000 at a treatment does of 15 mg/kg of mAb 34B5A.

Figure 6B:
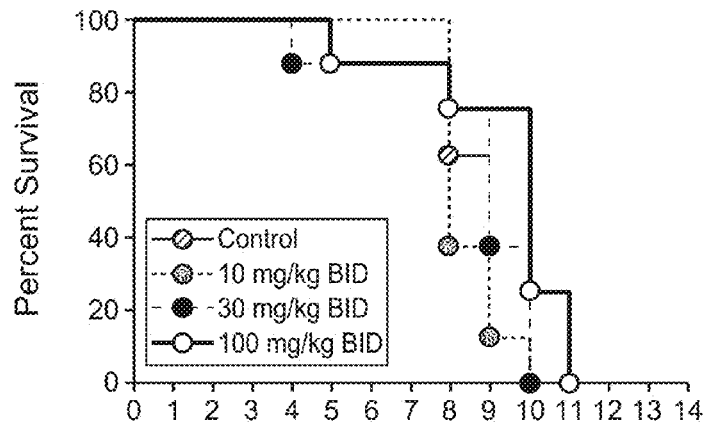

Parallel experiments were performed to compare efficacy of mAb 34B5A with that of oseltamivir phosphate. Oseltamivir phosphate was administered at 10 mg/kg, 30 mg/kg, or 100 mg/kg BID, beginning 72 hours post-virus infection. While oseltamivir phosphate did provide some protection to mice infected with influenza B virus B/Victoria/2000 compared to that of vehicle control treated animals, 100% mortality was observed by day 11, even at the highest dose administered. (See FIG. 6B.)

These results showed that monoclonal antibodies of the present invention are effective at treating influenza B virus infection in vivo. Additionally, these data showed that monoclonal antibodies of the present invention were effective at treating influenza B virus infection in vivo when administered up to at least 72 hours post influenza B virus infection. Taken together, these results additionally showed that monoclonal antibodies of the present invention displayed better in vivo efficacy in mice compared to that of oseltamivir phosphate when administered 72 hours post-virus infection.

Example 10. In Vivo Efficacy of mAb 34B5C in Mice Against Influenza B Virus B/Wisconsin/2010

The in vivo efficacy of mAb 34B5C to influenza B virus infection in mice was performed as follows. DBA/2J mice (Jackson Lab, Bar Harbor, Me.) were infected intra-nasally with 50 µl of influenza B virus strain B/Wisconsin/2010 diluted in influenza media (DMEM, 0.2% BSA, 2 µg/mL TPCK-treated trypsin) at the minimum $LD_{100}$ dose ($1 \times 10^6$ virus/mouse). Influenza virus infection was allowed to progress for either 48 hours or 72 hours prior to the intravenous administration of mAb 34B5C.

After 48 hours or 72 hours post influenza B virus B/Wisconsin/2010 infection, various amounts of mAb 34B5C were administered intravenously to the mice at a dose of 15 mg/kg, 5 mg/kg, and 1.7 mg/kg in 200 µl PBS. Control treated animals were administered mAb gD5237 at the highest tested equivalent dose of mAb 34B5C (i.e., approximately 15 mg/kg). Mice were monitored daily for body conditioning and survival, and also weighed daily, until 21 days after infection.

Figure 7A:
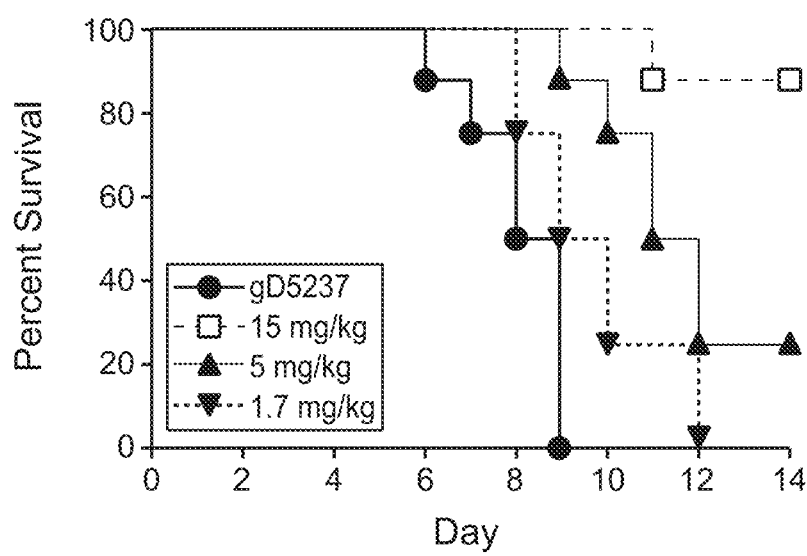
FIGS. 7A and 7B set forth data showing percent survival of mice infected with influenza B virus B/Wisconsin/2000 and administered various amounts of monoclonal antibody 34B5C at 48 hours post-infection or 72 hours post-infection, respectively.
Figure 7B:
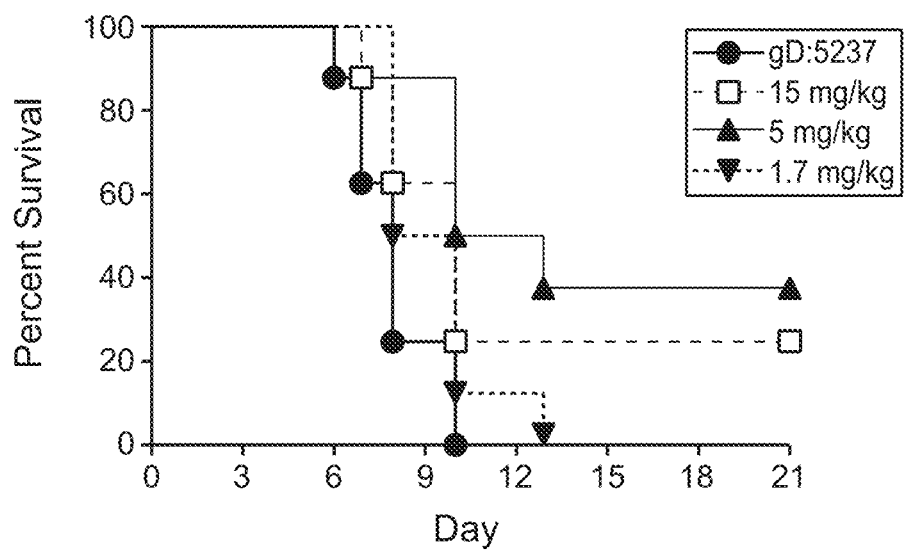

FIGS. 7A and 7B show percent survival (over time, in days) of mice administered various amounts of mAb 34B5C at 48 or 72 hours after infection with influenza B virus B/Wisconsin/2010, respectively. As shown in FIGS. 7A and 7B, 100% mortality was observed by day 9 or day 10 in infected mice administered control antibody. However, infected mice administered mAb 34B5C showed increased survival. (See FIGS. 7A and 7B.)

These results showed that monoclonal antibodies of the present invention are effective at treating various influenza B virus infections. Additionally, these data indicated that monoclonal antibodies of the present invention were effective at treating influenza B virus infection when administered up to at least 72 hours post influenza B virus infection.

Example 11. In Vivo Efficacy of mAb 46B8C in Mice Against Influenza B Virus B/Wisconsin/2010

To test the in vivo efficacy of mAb 46B8C in mice, the antibody was administered i.v. to mice infected with four different influenza B virus strains (B/Wisconsin/2010, B/Victoria/2000, B/Russia/1969, and B/Mass/1966). DBA/2J mice (Jackson Lab, Bar Harbor, Me.) were infected intranasally with 50 µl of different influenza B virus strains diluted into influenza media (DMEM, 0.2% BSA, 2 ug/mL TPCK treated trypsin) at $1 \times LD_{100}$ dose.

In one set of experiments, the following influenza B virus isolates were used: B/Wisconsin/2010, B/Victoria/2000, B/Russia/1969, and B/Mass/1966. At 24, 48, or 72 hours post infection, anti-hemagglutinin mAb 46B8C was administered intravenously at approximately 15 mg/kg in 200 µl PBS. Control treated animals were given mAb gD5237 (15 mg/kg). Mice were monitored for body conditioning and survival, and weighed until 21 days after infection.

Figure 8A:
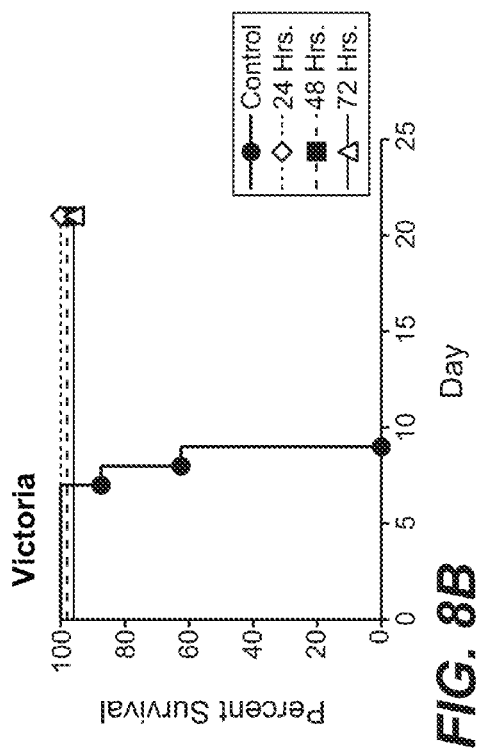
FIGS. 8A, 8B, 8C, and 8D set forth data showing percent survival of mice infected with influenza B viruses B/Wisconsin/2010, B/Victoria/2000, B/Russia/1969, and B/Massachusetts/1966, respectively, and administered monoclonal antibody 46B8C at 24, 48, or 72 hours post-infection.
Figure 8B:
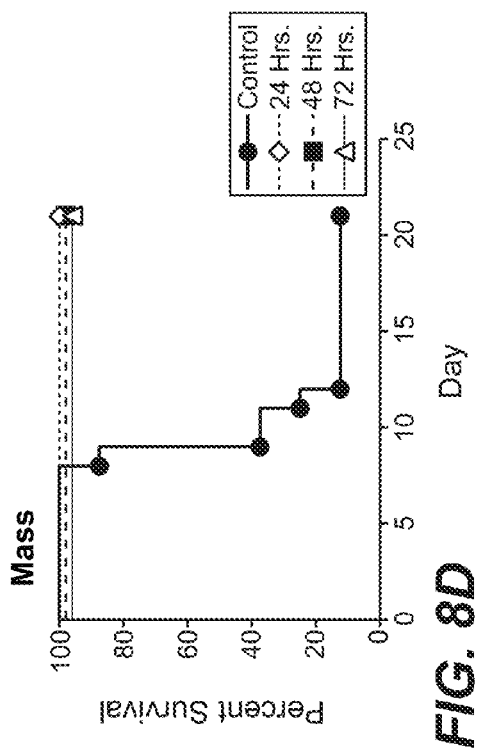
Figure 8C:
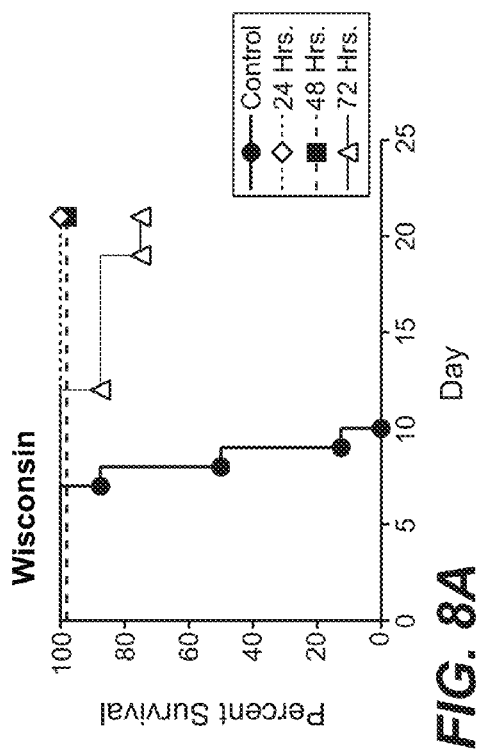
Figure 8D:
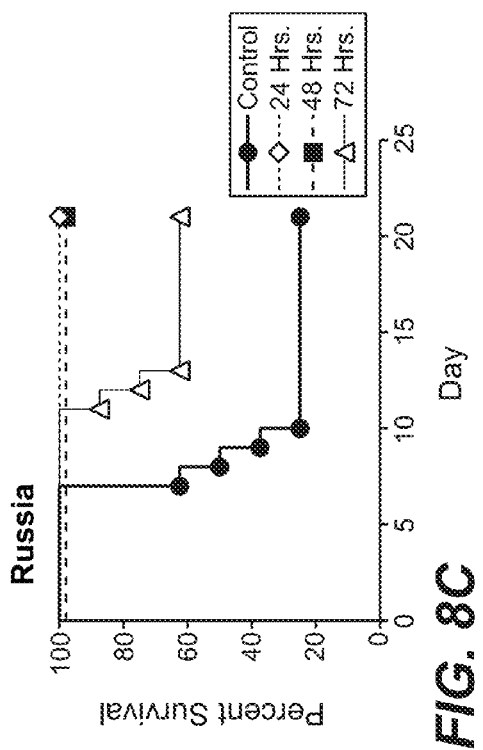

As shown in FIGS. 8A and 8B, 100% mortality was observed in the control treatment group by day 10 and day 9 in mice administered influenza B virus strain B/Wisconsin/2010 and B/Victoria/2000, respectively. A single dose of mAb 46B8C at 15 mg/kg administered at 24, 48, or 72 hours following infection with either B/Victoria/2000 or B/Mass/1966 resulted in 100% survival of the mice. (See FIGS. 8B and 8D.) A single dose of mAb 46B8C at 15 mg/kg administered at 24 or 48 hours after infection with either B/Wisconsin/2010 or B/Russia/1969 (as well as either B/Victoria/2000 or B/Mass/1966) resulted in 100% survival of the mice. (See FIGS. 8A, 8B, 8C, and 8D.)

These results showed that mAb 46B8C was effective at treating infection of various strains of influenza B virus in vivo. In particular, these results showed that mAb 46B8C was effective at treating influenza B virus infection and improving survival when administered at 24, 48, or 72 hours post-infection. Taken together, there results showed that monoclonal antibodies of the present invention were effective at treating influenza B virus isolates from ancestral, Yamagata, and Victoria lineages, even when administered up to at least 72 hours post-infection.

Example 12. In Vivo Efficacy of mAb 46B8C in Mice when Administered 72 Hours Post Influenza B Virus Infection The in vivo efficacy of various doses of mAb 46B8C to influenza B virus infection in mice was performed as follows. DBA/2J mice (Jackson Lab, Bar Harbor, Me.) were infected intranasally with 50 µl of influenza B virus strain B/Wisconsin/2010 or B/Victoria/2000 diluted in influenza media (DMEM, 0.2% BSA, 2 µg/mL TPCK-treated trypsin) at the minimum $LD_{100}$ dose. Influenza virus infection was allowed to progress for 72 hours prior to the intravenous administration of various doses of mAb 46B8C.

After 72 hours post influenza virus B infection, various amounts of mAb 46B8C were administered intravenously to the mice at a dose of 45 mg/kg, 15 mg/kg, or 5 mg/kg in 200 µl PBS. Control treated animals were administered mAb gD5237 at the highest tested equivalent dose of approximately 45 mg/kg. Mice were monitored daily for body conditioning and survival, and also weighed daily, until 21 days after infection.

Figure 9B:
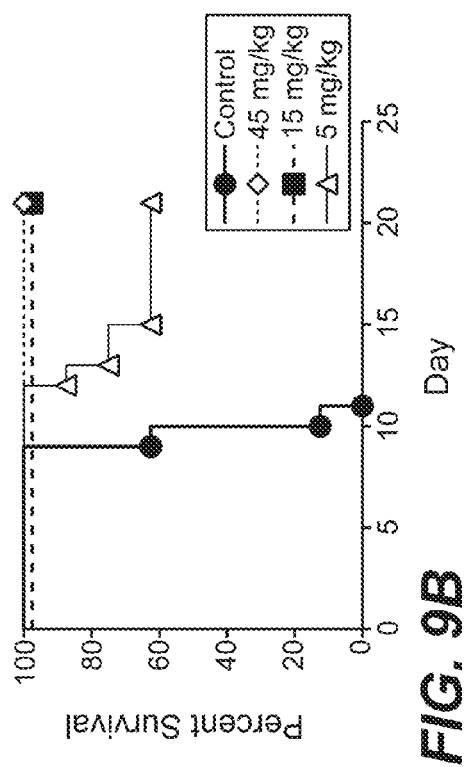
FIGS. 9A and 9B set forth data showing percent survival of mice infected with influenza B virus B/Wisconsin/2010 and B/Victoria/2000, respectively, and administered various amounts of monoclonal antibody 46B8C at 72 hours post-infection.
Figure 9A:
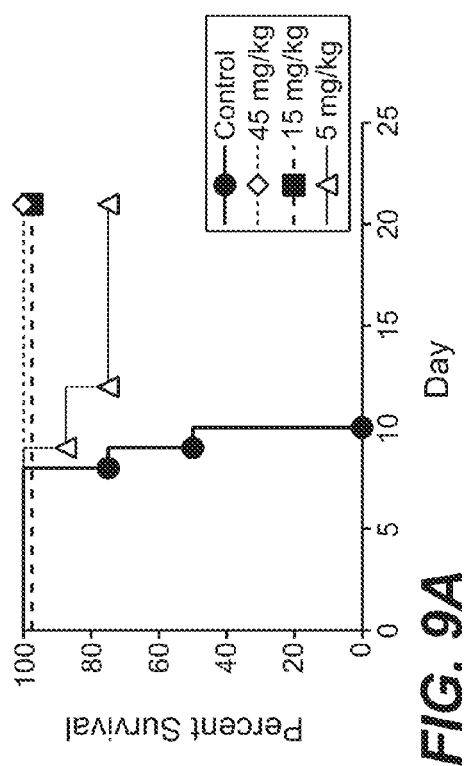

As shown in FIGS. 9A and 9B, administration of mAb 46B8C at either 45 mg/kg or 15 mg/kg at 72 hours post influenza B virus infection resulted in 100% survival of mice infected with either B/Wisconsin/2010 or B/Victoria/2000, respectively. Even at a dose of 5 mg/kg, administration of mAb 46B8C showed therapeutic treatment efficacy against influenza B virus B/Wisconsin/2010 and B/Victoria/2000 as measured by percent survival of the mice, as compared to control-treated animals. This data indicated that mAb 46B8C was effective at treating influenza B virus infection when administered at least up to 72 hours post influenza B virus infection.

Example 13. Comparison of In Vivo Efficacy of mAb 46B8C and Oseltamivir in Severe Influenza B Virus Infection in Mice To compare the efficacy of anti-influenza B virus hemagglutinin antibodies of the present invention to that of oseltamivir phosphate in mice, the following studies were performed. Balb/c mice (Charles River Laboratories, Hollister, Calif.) at 6-weeks old were infected intranasally with 50 µl influenza B virus strain B/Victoria/2000 at $4 \times LD_{100}$. At 48 hours post infection, anti-hemagglutinin antibody mAb 46B8C was administered as a single dose of 45 mg/kg or control IgG in 200 µl PBS intravenously. In these experiments, an oseltamivir dosing regimen consisting of 2 mg dosed twice daily (BID) for five days was compared with a single i.v. does of ~15 mg/kg of mAb 46B8C. (Oseltamivir phosphate) used in any of the Examples described herein was obtained from Toronto Research Chemicals, Cat. No. 0701000.)

Figure 10B:
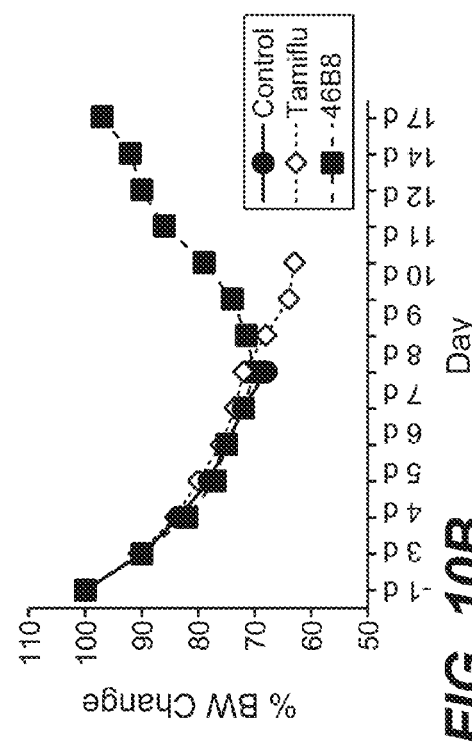
FIGS. 10A and 10B set forth data showing percent survival and percent body weight (BW) change, respectively, of mice infected with influenza B virus B/Victoria/2000 and administered either monoclonal antibody 46B8C or TAMIFLU® oseltamivir phosphate.
Figure 10A:
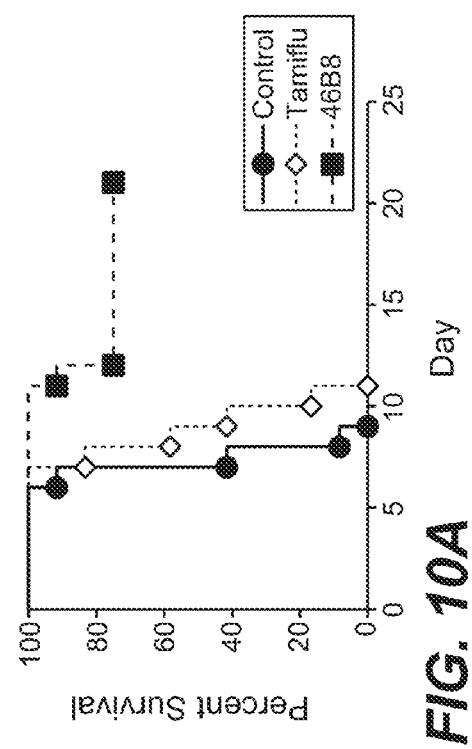

As shown in FIG. 10A, 100% mortality was observed by day 9 in control-IgG (mAb gD5237) treated animals, and 100% mortality was observed by day 11 in oseltamivir phosphate-treated animals. However, a single 15 mg/kg dose of mAb 46B8C protected approximately 75% of the infected animals from the lethal influenza B virus challenge. Additionally, animals treated with mAb 46B8C showed a recovery in % body weight change. (See FIG. 10B.)

Example 14. mAb 46B8C is Safe in Combination with TAMIFLU® Oseltamivir Phosphate and Reduces Lung Titer To further examine the use and efficacy of anti-influenza B virus hemagglutinin antibodies of the present invention to that of oseltamivir phosphate in mice, the following studies were performed. Balb/c mice (Charles River Laboratories, Hollister, Calif.) at 6-weeks old were infected intranasally with 50 µl influenza B virus strain B/Victoria/2000 at $1 \times LD_{100}$. At 48 hours post infection, anti-hemagglutinin antibody mAb 46B8C was administered as a single dose of 15 mg/kg or control IgG in 200 µl PBS intravenously. In these experiments, an oseltamivir dosing regimen consisting of 2 mg dosed twice daily (BID) for five days (100 mg/kg) was compared with a single i.v. does of ~15 mg/kg of mAb 46B8C. Combination treatment was also performed.

Figure 11A:
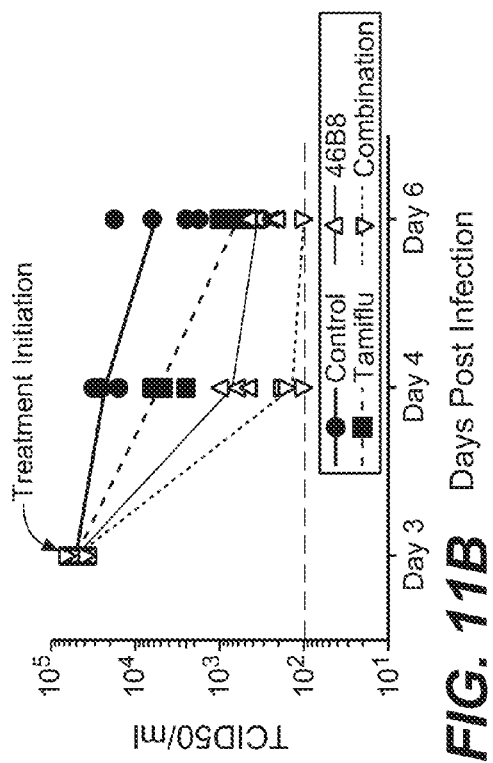
FIGS. 11A and 11B set forth data showing the effect of administration of monoclonal antibody 46B8C and TAMIFLU® oseltamivir phosphate alone or in combination on percent survival and viral lung titer, respectively, in mice.

As shown in FIG. 11A, 100% mortality was observed by day 11 in control-IgG (mAb gD5237) treated animals. However, a single 15 mg/kg dose of mAb 46B8C resulted in 100% survival of mice, when administered alone or in combination with oseltamivir phosphate. Additionally, treatment of animals with a combination of mAb 46B8C and oseltamivir phosphate was both safe and effective in this in vivo influenza B virus infection model.

Figure 11B:
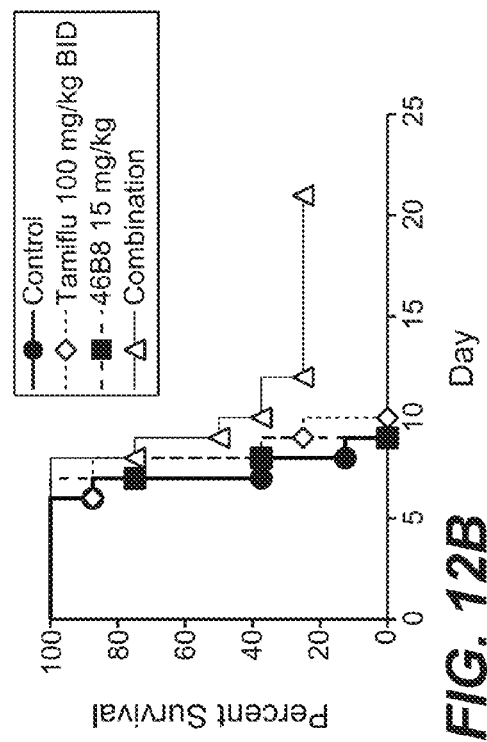

As shown in FIG. 11B, administration of mAb 46B8C, either alone or in combination with osletamivir phosphate, showed a reduction of influenza B virus lung titer compared to that observed in control-treated animals or in animals treated with oseltamivir phosphate alone.

These results indicated that monoclonal antibodies of the present invention are safe and effective when used in combination with neuraminidase inhibitors (e.g., oseltamivir).

Example 15. Synergy of mAb 46B8C with Oseltamivir in Severe Influenza B Virus Infection Model in Mice To further examine the efficacy of co-administration of anti-influenza B virus hemagglutinin antibodies of the present invention and oseltamivir phosphate in mice, the following studies were performed. Balb/c mice (Charles River Laboratories, Hollister, Calif.) at 6-weeks old were infected intranasally with 50 µl influenza B virus strain B/Victoria/2000 at $4 \times LD_{100}$. At 48 hours post infection, anti-hemagglutinin antibody mAb 46B8C was administered as a single dose of either 15 mg/kg or 5 mg/kg, or control IgG in 200 µl PBS intravenously. In these experiments, an oseltamivir dosing regimen consisting of 2 mg dosed twice daily (BID) for five days was compared with a single i.v. does of ~15 mg/kg of mAb 46B8C. In these experiments, an oseltamivir dosing regimen consisting of 2 mg dosed twice daily (BID) for five days (100 mg/kg). Animals were treated with either control antibody, mAb 46B8C alone, oseltamivir alone, or a combination of mAb 46B8C and oseltamivir.

Figure 12A:
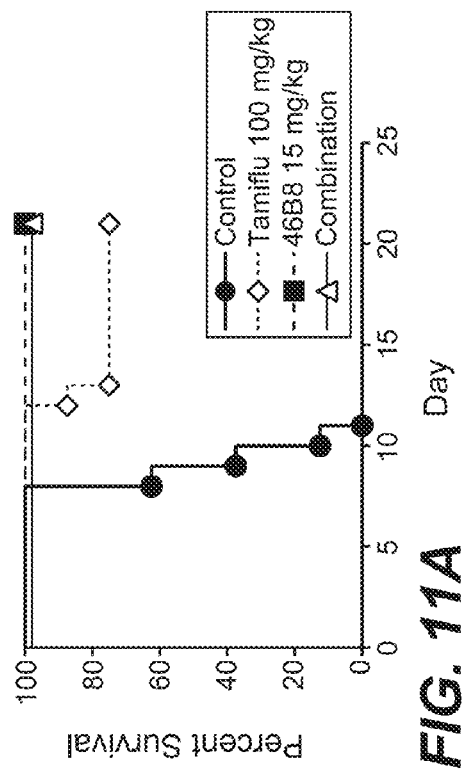
FIGS. 12A and 12B set forth data showing the effect of co-administration of monoclonal antibody 46B8C and TAMIFLU® oseltamivir phosphate.
Figure 12B:
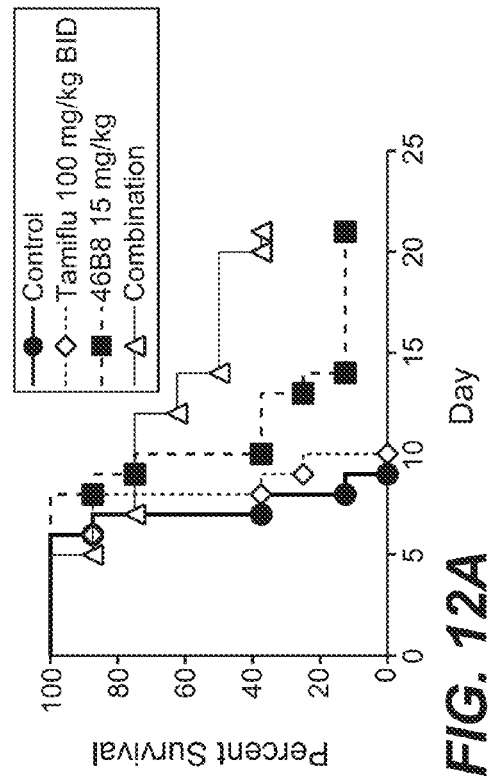
Figure 26A:
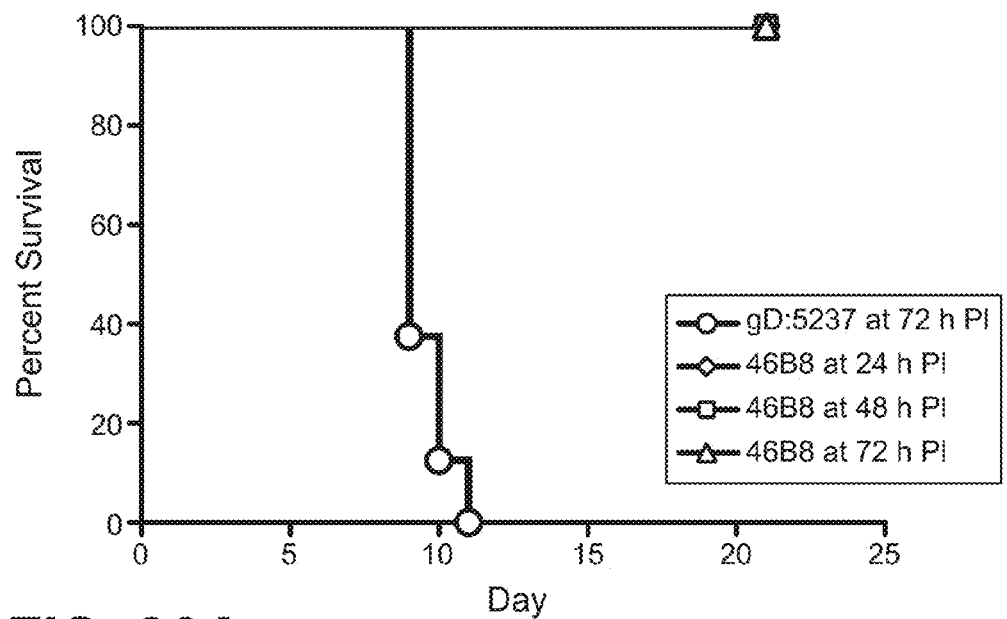
FIGS. 26A and 26B set forth data showing percent survival and percent body weight (BW) change, respectively, of mice infected with influenza B virus B/Brisbane/2008 and administered monoclonal antibody 46B8C.
Figure 26B:
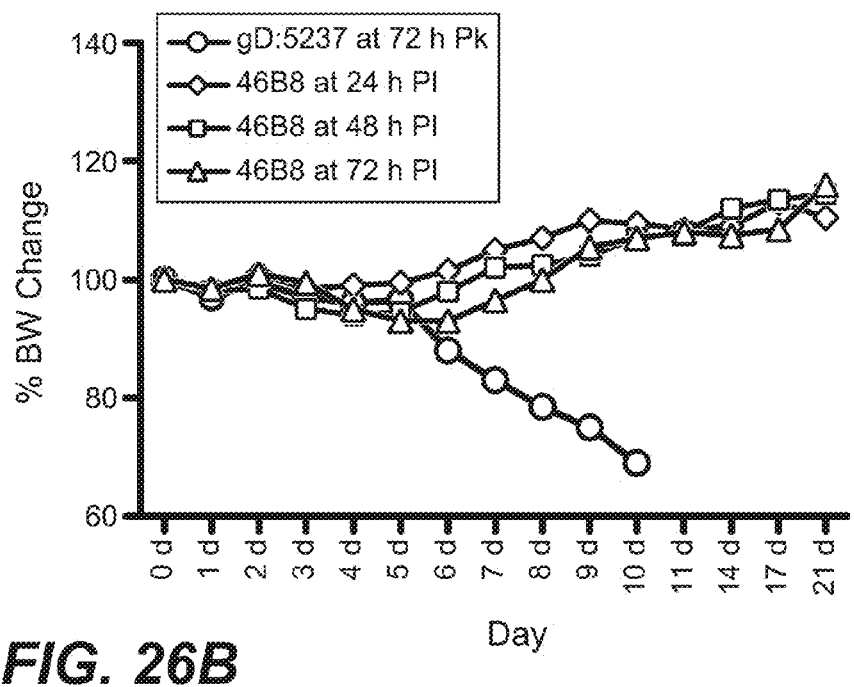

As shown in FIGS. 12A and 12B, animals administered with either control antibody or oseltamivir phosphate alone showed 100% mortality by day 9 or 10. Additionally, animals administered mAb 46B8C at 5 mg/kg showed 100% mortality by day 9 in this severe influenza B virus infection model. However, combination treatment of mAb 46B8C and oseltamivir phosphate resulted in increased survival at a dose of either 5 mg/kg or 15 mg/kg.

These results indicated that combination treatment using an antibody of the present invention together with oseltamivir provides some degree of synergy in treatment outcome compared to either treatment alone.

Example 16. Competition ELISA

Competition ELISA assays are developed using hemagglutinin influenza B virus (e.g., B/Victoria/2000, B/Wisconsin/2010, etc.). Hemagglutinin-coated ELISA plates are allowed to bind test antibody at various concentrations (X-axis) prior to the addition of saturating concentrations of biotin labeled monoclonal antibody of the present invention (e.g., mAb 48B8C, etc). If the test antibody competed for the influenza B virus hemagglutinin epitope of a monoclonal antibody of the present invention, the biotin ELISA signal (Y-axis) is decreased as a function of increasing test antibody concentration. The binding data are fit with a nonlinear dose response curve to determine the $EC_{50}$ value given in nM.

Monoclonal antibody of the present invention is biotinylated through amine coupling according to the manufacturer's recommended protocol (Sulfo-NHS-LC-LC, Pierce, Rockford, Ill.). Final stock concentration of the biotinylated mAb is, for example, 13.2 mM. To determine the optimal concentration for usage, the biotinylated mAb is serially titrated against immobilized hemagglutinin from influenza B virus. Recombinant hemagglutinin proteins are diluted to 2 μg/ml in phosphate buffered saline (PBS) and dispensed (100 μl) onto 96-well Nunc Maxisorp plates (Nunc, Rochester, N.Y.). The plates are coated overnight at 4° C., rinsed in PBS, and then blocked for 1-hour at room temperature with PBS containing 1% bovine serum albumin (BSA, Sigma-Aldrich, St. Louis, Mo.).

Each plate then receives 100 μl of serially diluted biotinylated mAb starting at an initial concentration of 88 nM with 1/3 dilutions in PBS containing 1.0% BSA and 0.05% Polysorbate 20 (Sigma-Aldrich). After one hour incubation, the plates are washed and then incubated with 100 μl of a 1:5000 dilution of streptavidin-conjugated horseradish peroxidase (Caltag Laboratories, Carlsbad, Calif.) for 30 minutes at room temperature. Following the incubation, the plates are washed and developed with 100 μl of TMB substrate (Kirkegaard and Perry Laboratories, Inc. Gaithersburg, Md.). Plates are read on a SpectraMax plate reader (Molecular Devices, Sunnyvale, Calif.) at O.D. 450 nM. The optimal concentration of biotinylated mAb is determined to be, for example, 1 nM.

Example 17. In Vivo Efficacy of mAb 46B8C in Mice Against Influenza B Virus B/Brisbane/2008

To test the in vivo efficacy of mAb 46B8C in mice against influenza B virus B/Brisbane/2008, an influenza B virus of Victoria lineage (Viapur, LLC, San Diego, Calif.), the following studies were performed. DBA/2J mice were infected intranasally with a minimum of $1\times LD_{100}$ dose ($1\times 10^4$ PFU/mouse) of influenza B virus B/Brisbane/2008. At 24, 48, and 72 hours post-infection, 8 female mice/group were administered intravenously mAb 46B8C at 15 mg/kg in 0.1 mL PBS. Mice were monitored for survival, and weighed until 21 days post-infection. As a control, a group of infected mice were treated with human IgG1 antibody anti-gD (no known target in mouse) at 15 mg/kg 72 hours post-infection.

As shown in FIG. 26A, 100% mortality was observed in the control treatment group by day 11 in mice administered influenza B virus B/Brisbane/2008. A single dose of mAb 46B8C at 15 mg/kg administered at 24, 48, or 72 hours following infection with influenza B virus B/Brisbane/2008 resulted in 100% survival of the mice. (See FIG. 26A.) FIG. 26B shows changes in body weight in the mice under the various conditions and treatments described above.

These results showed that mAb 46B8C was effective at treating infection of influenza B virus B/Brisbane/2008, from the Victoria lineage.

Statistical Analyses

Statistics were calculated using JMP version 9.0.2 software (SAS Institute). Survival experiments were compared using log-rank test. P values <0.05 were considered significant. $IC_{50}$ curves and values were plotted and calculated using Graphpad Prism version 5.0 software.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for treating or inhibiting influenza B virus infection in an individual in need thereof, the method comprising administering to the individual an effective amount of a composition comprising an anti-hemagglutinin monoclonal antibody that specifically binds influenza B virus hemagglutinin, wherein the antibody comprises three heavy chain hypervariable regions (HVR-H1, HVR-H2, and HVR-H3) and three light chain hypervariable regions (HVR-L1, HVR-L2, and HVR-L3), wherein:
    (a) HVR-H1 comprises the amino acid sequence of SEQ ID NO:63;
    (b) HVR-H2 comprises the amino acid sequence of SEQ ID NO: 69;
    (c) HVR-H3 comprises the amino acid sequence of SEQ ID NO:77;
    (d) HVR-L1 comprises the amino acid sequence of SEQ ID NO:56;
    (e) HVR-L2 comprises the amino acid sequence of SEQ ID NO:58; and
    (f) HVR-L3 comprises the amino acid sequence of SEQ ID NO:60,
thereby treating or inhibiting influenza B virus infection in the individual.

2. The method of claim 1, wherein the antibody comprises a heavy chain variable region and a light chain variable region, wherein the heavy chain variable region comprises the amino acid sequence of SEQ ID NO:97, and the light chain variable region comprises the amino acid sequence of SEQ ID NO:91.

3. The method of claim 1, wherein the antibody comprises a heavy chain and a light chain, wherein the heavy chain comprises the amino acid sequence of SEQ ID NO:98, and the light chain comprises the amino acid sequence of SEQ ID NO:93.

4. The method of claim 1, claim 2, or claim 3, wherein the method further comprises administering to the individual an additional therapeutic agent.

5. The method of claim 4, wherein the additional therapeutic agent is a neuraminidase inhibitor, an anti-hemagglutinin antibody that binds influenza B virus hemagglutinin, or an anti-M2 antibody that binds influenza B virus M2 protein.

6. The method of claim 4, wherein the additional therapeutic agent is a neuraminidase inhibitor selected from the group consisting of oseltamivir, zanamivir, amantadine, and rimatadine.

7. The method of claim 1, claim 2, or claim 3, wherein the individual is a human.

8. The method of claim 5, wherein the anti-hemagglutinin monoclonal antibody and the additional therapeutic agent are administered to the individual simultaneously or sequentially.

9. The method of claim 5, wherein the additional therapeutic agent is administered to the individual prior to administration of the anti-hemagglutinin monoclonal antibody.

10. The method of claim 5, wherein the additional therapeutic agent is administered to the individual at the same time as administration of the anti-hemagglutinin monoclonal antibody.

11. The method of claim 5, wherein the anti-hemagglutinin monoclonal antibody is administered to the individual prior to administration of the additional therapeutic agent.

12. The method of claim 1, claim 2, or claim 3, wherein the anti-hemagglutinin monoclonal antibody is administered to the individual at about 12 hours after onset of symptoms of influenza virus infection, at about 24 hours after onset of symptoms of influenza virus infection, at about 36 hours after onset of symptoms of influenza virus infection, at about 48 hours after onset of symptoms of influenza virus infection, at about 60 hours after onset of symptoms of influenza virus infection, at about 72 hours after onset of symptoms of influenza virus infection, at about 84 hours after onset of symptoms of influenza virus infection, or at about 96 hours after onset of symptoms of influenza virus infection.

13. The method of claim 1, claim 2, or claim 3, wherein the anti-hemagglutinin monoclonal antibody is administered to the individual between about 24 hours and 48 hours after onset of symptoms of influenza virus infection, between about 48 hours and 72 hours after onset of symptoms of influenza virus infection, or between about 72 hours and 96 hours after onset of symptoms of influenza virus infection.

14. The method of claim 1, claim 2, or claim 3, wherein the anti-hemagglutinin monoclonal antibody is administered by parenteral, intrapulmonary, or intranasal administration.

15. The method of claim 14, wherein the parenteral administration is selected from the group consisting of intramuscular administration, intravenous administration, intraarterial administration, intraperitoneal administration, and subcutaneous administration.

* * * * *

SEQUENCE LISTING

```
<160> NUMBER OF SEQ ID NOS: 108

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaagtagtcc ttgaccaggc ag                                          22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 2
ctcagcgtca gggtgytgct gag                                        23

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggtktggts gtctccac                                              18

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caggtgcagc tggtgcagtc tggggc                                     26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caggtccagc tggtgcagtc tggggc                                     26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caggtcacct tgaaggagtc tggtcc                                     26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaggtgcagc tggtggagtc tggggg                                     26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 8
caggtgcagc tgcaggagtc gggccc                                              26

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gaggtgcagc tggtgcagtc tgg                                                 23

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caggtacagc tgcagcagtc aggtcc                                              26

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caggtgcagc tggtgcaatc tgg                                                 23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ghcatccrgw tgacccagtc tc                                                  22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gatrttgtga tgacycagwc tc                                                  22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
```
gaaatwgtrw tgacrcagtc tc                                          22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gacatcgtga tgacccagtc tcc                                         23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaaacgacac tcacgcagtc tc                                          22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gawrttgtgm tgacwcagtc tc                                          22

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagtctgtgy tgackcagcc rccctc                                      26

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagtctgccc tgactcagcc t                                           21

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcctatgagc tgacwcagsh vccckc                                              26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cagcctgtgc tgactcartc vccctc                                              26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cagcctgtgc tgactcagcc aacttc                                              26

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aattttatgc tgactcagcc ccac                                                24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
caggctgtgg tgactcagga gccc                                                24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cagactgtgg tgacccagga gcc                                                 23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagcctgtgc tgactcagcc acc                                                 23

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 27
gcagcccagg gcsgctgtgc                                              20

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 28
gcacacaaca gaggcagttc cag                                          23

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 29
cttgragctc ctcagaggag                                              20

<210> SEQ ID NO 30
<211> LENGTH: 98
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 30
ccaccatggg atggtcatgt atcatccttt ttctagtagc aactgcaact ggagtacatt   60
cacaggtgca gctggtgcag tctggggctg aggtgaag                          98

<210> SEQ ID NO 31
<211> LENGTH: 98
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 31
ccaccatggg atggtcatgt atcatccttt ttctagtagc aactgcaact ggagtacatt   60
cacagatcac cttgaaggag tctggtccta cgctggtg                          98

<210> SEQ ID NO 32
<211> LENGTH: 98
<212> TYPE: DNA
<213> ORGANISM: Artificial Sequence
<220> FEATURE:
<223> OTHER INFORMATION: Description of Artificial Sequence: Synthetic
     primer

```
<400> SEQUENCE: 32
ccaccatggg atggtcatgt atcatccttt ttctagtagc aactgcaact ggagtacatt      60
cacaggtgca gctggtggag tctggggggag gcgtggtc                            98

<210> SEQ ID NO 33
<211> LENGTH: 95
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccaccatggg atggtcatgt atcatccttt ttctagtagc aactgcaact ggagtacatt      60
cagaggtgca gctggtggag tctgggggag gcttg                                95

<210> SEQ ID NO 34
<211> LENGTH: 96
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccaccatggg atggtcatgt atcatccttt ttctagtagc aactgcaact ggagtacatt      60
cacaggtgca gctgcaggag tcgggcccag gactgg                               96

<210> SEQ ID NO 35
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ccaccatggg atggtcatgt atcatccttt ttctagtagc aactgcaact ggagtacatt      60
cagaggtgca gctggtgcag tctggagcag aggtgaaaaa g                         101

<210> SEQ ID NO 36
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccaccatggg atggtcatgt atcatccttt ttctagtagc aactgcaact ggagtacatt      60
cacaggtaca gctgcagcag tcaggtccag gact                                 94

<210> SEQ ID NO 37
<211> LENGTH: 95
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccaccatggg atggtcatgt atcatccttt ttctagtagc aactgcaact ggagtacatt      60
```

```
cacaggtgca gctggtgcaa tctgggtctg agttg                           95

<210> SEQ ID NO 38
<211> LENGTH: 95
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccaccatggg atggtcatgt atcatccttt ttctagtagc aactgcaact ggagtacatt   60
cagacatcca gatgacccag tctccatcct ccctg                              95

<210> SEQ ID NO 39
<211> LENGTH: 95
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccaccatggg atggtcatgt atcatccttt ttctagtagc aactgcaact ggagtacatt   60
cagatattgt gatgactcag tctcactctc cctgc                              95

<210> SEQ ID NO 40
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
ccaccatggg atggtcatgt atcatccttt ttctagtagc aactgcaact ggagtacatt   60
cagaaattgt gttgacacag tctccagcca ccctgtcttt g                      101

<210> SEQ ID NO 41
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ccaccatggg atggtcatgt atcatccttt ttctagtagc aactgcaact ggagtacatt   60
cagacatcgt gatgacccag tctccagact ccctggctgt g                      101

<210> SEQ ID NO 42
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccaccatggg atggtcatgt atcatccttt ttctagtagc aactgcaact ggagtacatt   60
cagaaacgac actcacgcag tctccagc                                      88

<210> SEQ ID NO 43
```

```
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccaccatggg atggtcatgt atcatccttt ttctagtagc aactgcaact ggagtacatt    60
cagaaattgt gctgactcag tctccagact ttcg                                94

<210> SEQ ID NO 44
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccaccatggg atggtcatgt atcatccttt ttctagtagc aactgcaact ggagtacatt    60
cacagtctgt gytgackcag ccrccctc                                       88

<210> SEQ ID NO 45
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccaccatggg atggtcatgt atcatccttt ttctagtagc aactgcaact ggagtacatt    60
cacagtctgc cctgactcag cct                                            83

<210> SEQ ID NO 46
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccaccatggg atggtcatgt atcatccttt ttctagtagc aactgcaact ggagtacatt    60
catcctatga gctgacwcag shvccckc                                       88

<210> SEQ ID NO 47
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccaccatggg atggtcatgt atcatccttt ttctagtagc aactgcaact ggagtacatt    60
cacagcctgt gctgactcar tcvccctc                                       88

<210> SEQ ID NO 48
<211> LENGTH: 88
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 48
ccaccatggg atggtcatgt atcatccttt ttctagtagc aactgcaact ggagtacatt    60
cacagcctgt gctgactcag ccaacttc                                       88

<210> SEQ ID NO 49
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccaccatggg atggtcatgt atcatccttt ttctagtagc aactgcaact ggagtacatt    60
caaattttat gctgactcag ccccac                                         86

<210> SEQ ID NO 50
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccaccatggg atggtcatgt atcatccttt ttctagtagc aactgcaact ggagtacatt    60
cacaggctgt ggtgactcag gagccc                                         86

<210> SEQ ID NO 51
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccaccatggg atggtcatgt atcatccttt ttctagtagc aactgcaact ggagtacatt    60
cacagactgt ggtgacccag gagcc                                          85

<210> SEQ ID NO 52
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccaccatggg atggtcatgt atcatccttt ttctagtagc aactgcaact ggagtacatt    60
cacagcctgt gctgactcag ccacc                                          85

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gccaggggga agaccgatg                                              19

<210> SEQ ID NO 54
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctgggataga agttattcag caggcacaca acagaagcag ttccagattt caactgctc     59

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Gly Ser Thr Ser Asp Ile Gly Ser Tyr Asn Tyr Val Ser
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Ser Gln Ser Leu Leu Arg Ser Asn Gly Tyr Asn Tyr Leu Asp
1               5                   10                  15

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Val Ser Gln Arg Pro Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Gly Ser Asn Arg Ala Ser
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Ala Ser Tyr Ala Gly Asn Asn Ile Tyr Val
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Gln Ala Leu Gln Thr Pro Tyr Thr
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Tyr Tyr Ile His
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala His His Met His
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Gln Trp Ile Gly
1               5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ile Asp Pro Asn Gly Ser Gly Thr Thr Tyr Ala Gln Lys Phe Gln
1               5                   10                  15

Gly

```
<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Ile Asp Pro Asn Gly Ala Gly Thr Thr Tyr Ala Gln Lys Phe Gln
1               5                   10                  15

Gly

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Ile Asp Pro Asn Asn Asp Gly Thr Ile Tyr Ala Gln Lys Phe Gln
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met Met Tyr Pro Gly Asp Ser Asp Thr Ile Tyr Ser Pro Ser Phe Gln
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Met Tyr Pro Gly Asp Ala Asp Ala Ile Tyr Ser Pro Ser Phe Gln
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Met Tyr Pro Gly Glu Ser Glu Thr Ile Tyr Ser Pro Ser Phe Gln
1               5                   10                  15

Gly
```

```
<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Met Met Tyr Pro Gly Asp Ala Asp Thr Ile Tyr Ser Pro Ser Phe Gln
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Met Met Tyr Pro Gly Ser Ser Asp Thr Ile Tyr Ser Pro Ser Phe Gln
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Met Met Tyr Pro Gly Asp Ser Asp Ala Ile Tyr Ser Pro Ser Phe Gln
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Met Met Tyr Pro Gly Asp Thr Asp Thr Ile Tyr Ser Pro Ser Phe Gln
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Met Met Tyr Pro Gly Glu Ser Asp Thr Ile Tyr Ser Pro Ser Phe Gln
1               5                   10                  15
```

Gly

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Asp Trp Asn Phe Asp Leu Tyr Leu Gly Trp Phe Asp Pro
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Trp Ala Trp Asn Phe Asp Phe Phe Leu Gly Trp Phe Asp Pro
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Pro Gly Tyr Ser Gly Tyr His Tyr Gly Trp Phe Asp Thr
1               5                   10

<210> SEQ ID NO 78
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Val Leu Thr Gln Pro Pro Ser Ala Ser Gly Ser Arg Gly Gln
1               5                   10                  15

Ser Ile Thr Ile Ser Cys Thr Gly Ser Thr Ser Asp Ile Gly Ser Tyr
            20                  25                  30

Asn Tyr Val Ser Trp Tyr Gln Gln His Pro Gly Thr Ala Pro Lys Val
        35                  40                  45

Ile Leu Tyr Glu Val Ser Gln Arg Pro Ser Gly Val Pro Asp Arg Phe
    50                  55                  60

Ser Gly Ser Lys Ser Gly Asn Thr Ala Phe Leu Thr Val Ser Gly Leu
65                  70                  75                  80

Gln Thr Asp Asp Glu Ala Asp Tyr Tyr Cys Ala Ser Tyr Ala Gly Asn
                85                  90                  95

Asn Ile Tyr Val Phe Gly Ser Gly Thr Lys Val Thr
            100                 105

<210> SEQ ID NO 79
<211> LENGTH: 123

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Tyr Ile His Trp Val Arg Gln Ala Pro Gly Gln Gly Leu Glu Trp Met
        35                  40                  45

Gly Arg Ile Asp Pro Asn Gly Ser Gly Thr Thr Tyr Ala Gln Lys Phe
    50                  55                  60

Gln Gly Arg Val Thr Leu Thr Met Asp Thr Ser Ile Thr Thr Ala Tyr
65                  70                  75                  80

Met Glu Leu Ser Arg Leu Arg Phe Asp Asp Thr Ala Ile Tyr Tyr Cys
                85                  90                  95

Ala Arg Trp Asp Trp Asn Phe Asp Leu Tyr Leu Gly Trp Phe Asp Pro
            100                 105                 110

Trp Gly Gln Gly Thr Pro Val Thr Val Ala Ser
        115                 120

<210> SEQ ID NO 80
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Ser Val Leu Thr Gln Pro Pro Ser Ala Ser Gly Ser Arg Gly Gln
1               5                   10                  15

Ser Ile Thr Ile Ser Cys Thr Gly Ser Thr Ser Asp Ile Gly Ser Tyr
            20                  25                  30

Asn Tyr Val Ser Trp Tyr Gln Gln His Pro Gly Thr Ala Pro Lys Val
        35                  40                  45

Ile Leu Tyr Glu Val Ser Gln Arg Pro Ser Gly Val Pro Asp Arg Phe
    50                  55                  60

Ser Gly Ser Lys Ser Gly Asn Thr Ala Phe Leu Thr Val Ser Gly Leu
65                  70                  75                  80

Gln Thr Asp Asp Glu Ala Asp Tyr Tyr Cys Ala Ser Tyr Ala Gly Asn
                85                  90                  95

Asn Ile Tyr Val Phe Gly Ser Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

```
Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 81
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Tyr Ile His Trp Val Arg Gln Ala Pro Gly Gln Gly Leu Glu Trp Met
        35                  40                  45

Gly Arg Ile Asp Pro Asn Gly Ser Gly Thr Thr Tyr Ala Gln Lys Phe
    50                  55                  60

Gln Gly Arg Val Thr Leu Thr Met Asp Thr Ser Ile Thr Thr Ala Tyr
65                  70                  75                  80

Met Glu Leu Ser Arg Leu Arg Phe Asp Asp Thr Ala Ile Tyr Tyr Cys
                85                  90                  95

Ala Arg Trp Asp Trp Asn Phe Asp Leu Tyr Leu Gly Trp Phe Asp Pro
            100                 105                 110

Trp Gly Gln Gly Thr Pro Val Thr Val Ala Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
                450

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ser Val Leu Thr Gln Pro Pro Ser Ala Ser Gly Ser Arg Gly Gln Ser
1               5                   10                  15

Ile Thr Ile Ser Cys Thr Gly Ser Thr Ser Asp Ile Gly Ser Tyr Asn
                20                  25                  30

Tyr Val Ser Trp Tyr Gln Gln His Pro Gly Thr Ala Pro Lys Val Ile
            35                  40                  45

Leu Tyr Glu Val Ser Gln Arg Pro Ser Gly Val Pro Asp Arg Phe Ser
    50                  55                  60

Gly Ser Lys Ser Gly Asn Thr Ala Phe Leu Thr Val Ser Gly Leu Gln
65                  70                  75                  80

Ala Glu Asp Glu Ala Asp Tyr Tyr Cys Ala Ser Tyr Ala Gly Asn Asn
                85                  90                  95

Ile Tyr Val Phe Gly Ser Gly Thr Lys Val Thr
            100                 105

<210> SEQ ID NO 83
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
                20                  25                  30

Tyr Ile His Trp Val Arg Gln Ala Pro Gly Gln Gly Leu Glu Trp Met
            35                  40                  45

Gly Arg Ile Asp Pro Asn Gly Ala Gly Thr Thr Tyr Ala Gln Lys Phe
    50                  55                  60
```

-continued

Gln Gly Arg Val Thr Leu Thr Met Asp Thr Ser Ile Thr Thr Ala Tyr
65                  70                  75                  80

Met Glu Leu Ser Arg Leu Arg Phe Asp Asp Thr Ala Ile Tyr Tyr Cys
                85                  90                  95

Ala Arg Trp Asp Trp Asn Phe Asp Leu Tyr Leu Gly Trp Phe Asp Pro
            100                 105                 110

Trp Gly Gln Gly Thr Pro Val Thr Val Ala Ser
        115                 120

<210> SEQ ID NO 84
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ser Val Leu Thr Gln Pro Pro Ser Ala Ser Gly Ser Arg Gly Gln Ser
1               5                   10                  15

Ile Thr Ile Ser Cys Thr Gly Ser Thr Ser Asp Ile Gly Ser Tyr Asn
                20                  25                  30

Tyr Val Ser Trp Tyr Gln Gln His Pro Gly Thr Ala Pro Lys Val Ile
            35                  40                  45

Leu Tyr Glu Val Ser Gln Arg Pro Ser Gly Val Pro Asp Arg Phe Ser
        50                  55                  60

Gly Ser Lys Ser Gly Asn Thr Ala Phe Leu Thr Val Ser Gly Leu Gln
65                  70                  75                  80

Ala Glu Asp Glu Ala Asp Tyr Tyr Cys Ala Ser Tyr Ala Gly Asn Asn
                85                  90                  95

Ile Tyr Val Phe Gly Ser Gly Thr Lys Val Thr Val Leu Gly Gln Pro
            100                 105                 110

Lys Ala Asn Pro Thr Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 85
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Gln Ser Gly Ala Glu Val Lys Lys Pro Gly Ala
1               5                   10                  15

```
Ser Val Lys Val Ser Cys Lys Ala Ser Gly Tyr Ile Phe Thr Gly Tyr
         20                  25                  30

Tyr Ile His Trp Val Arg Gln Ala Pro Gly Gln Gly Leu Glu Trp Met
         35                  40                  45

Gly Arg Ile Asp Pro Asn Gly Ala Gly Thr Thr Tyr Ala Gln Lys Phe
 50                  55                  60

Gln Gly Arg Val Thr Leu Thr Met Asp Thr Ser Ile Thr Thr Ala Tyr
 65                  70                  75                  80

Met Glu Leu Ser Arg Leu Arg Phe Asp Asp Thr Ala Ile Tyr Tyr Cys
             85                  90                  95

Ala Arg Trp Asp Trp Asn Phe Asp Leu Tyr Leu Gly Phe Asp Pro
                100                 105                 110

Trp Gly Gln Gly Thr Pro Val Thr Val Ala Ser Ala Ser Thr Lys Gly
             115                 120                 125

Pro Ser Val Phe Pro Leu Ala Pro Ser Ser Lys Ser Thr Ser Gly Gly
         130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430
```

```
Met His Glu Ala Leu His Asn His Tyr Thr Gln Lys Ser Leu Ser Leu
            435                 440                 445

Ser Pro Gly Lys
        450

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ser Ala Leu Thr Gln Pro Pro Ser Ala Ser Gly Ser Arg Gly Gln Ser
1               5                   10                  15

Ile Thr Ile Ser Cys Thr Gly Ser Thr Ser Asp Ile Gly Ser Tyr Asn
            20                  25                  30

Tyr Val Ser Trp Tyr Gln Gln His Pro Gly Thr Ala Pro Lys Val Ile
        35                  40                  45

Leu Tyr Glu Val Ser Gln Arg Pro Ser Gly Val Pro Asp Arg Phe Ser
    50                  55                  60

Gly Ser Lys Ser Gly Asn Thr Ala Phe Leu Thr Val Ser Gly Leu Gln
65                  70                  75                  80

Ala Glu Asp Glu Ala Asp Tyr Tyr Cys Ala Ser Tyr Ala Gly Asn Asn
                85                  90                  95

Ile Tyr Val Phe Gly Ser Gly Thr Lys Val Thr
            100                 105

<210> SEQ ID NO 87
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ser Ala Leu Thr Gln Pro Pro Ser Ala Ser Gly Ser Arg Gly Gln Ser
1               5                   10                  15

Ile Thr Ile Ser Cys Thr Gly Ser Thr Ser Asp Ile Gly Ser Tyr Asn
            20                  25                  30

Tyr Val Ser Trp Tyr Gln Gln His Pro Gly Thr Ala Pro Lys Val Ile
        35                  40                  45

Leu Tyr Glu Val Ser Gln Arg Pro Ser Gly Val Pro Asp Arg Phe Ser
    50                  55                  60

Gly Ser Lys Ser Gly Asn Thr Ala Phe Leu Thr Val Ser Gly Leu Gln
65                  70                  75                  80

Ala Glu Asp Glu Ala Asp Tyr Tyr Cys Ala Ser Tyr Ala Gly Asn Asn
                85                  90                  95

Ile Tyr Val Phe Gly Ser Gly Thr Lys Val Thr Val Leu Gly Gln Pro
            100                 105                 110

Lys Ala Asn Pro Thr Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160
```

```
Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Lys
            180                 185                 190

Ser Tyr Ser Cys Gln Val Thr His Glu Gly Ser Thr Val Glu Lys Thr
            195                 200                 205

Val Ala Pro Thr Glu Cys Ser
            210                 215

<210> SEQ ID NO 88
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Tyr Ile His Trp Val Arg Gln Ala Pro Gly Gln Gly Leu Glu Trp Met
            35                  40                  45

Gly Arg Ile Asp Pro Asn Gly Ala Gly Thr Thr Tyr Ala Gln Lys Phe
    50                  55                  60

Gln Gly Arg Val Thr Leu Thr Met Asp Thr Ser Ile Thr Thr Ala Tyr
65                  70                  75                  80

Met Glu Leu Ser Arg Leu Arg Phe Asp Asp Thr Ala Ile Tyr Tyr Cys
                85                  90                  95

Ala Arg Trp Asp Trp Asn Phe Asp Leu Tyr Leu Gly Trp Phe Asp Pro
            100                 105                 110

Trp Gly Gln Gly Thr Pro Val Thr Val Ala Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 89
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ala His
            20                  25                  30

His Met His Trp Val Arg Gln Ala Pro Gly Gln Gly Leu Gly Trp Met
        35                  40                  45

Gly Trp Ile Asp Pro Asn Asn Asp Gly Thr Ile Tyr Ala Gln Lys Phe
    50                  55                  60

Gln Gly Arg Val Thr Leu Thr Met Asp Thr Ser Ile His Thr Ala Tyr
65                  70                  75                  80

Met Glu Leu Ser Gly Leu Arg Tyr Asp Asp Thr Ala Ile Tyr Tyr Cys
                85                  90                  95

Val Arg Trp Ala Trp Asn Phe Asp Phe Phe Leu Gly Trp Phe Asp Pro
            100                 105                 110

Trp Gly Gln Gly Thr Leu Val Thr Val Ala Ser
        115                 120

<210> SEQ ID NO 90
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Asn Ala His
            20                  25                  30

His Met His Trp Val Arg Gln Ala Pro Gly Gln Gly Leu Gly Trp Met
        35                  40                  45

Gly Trp Ile Asp Pro Asn Asn Asp Gly Thr Ile Tyr Ala Gln Lys Phe
    50                  55                  60

Gln Gly Arg Val Thr Leu Thr Met Asp Thr Ser Ile His Thr Ala Tyr
65                  70                  75                  80

Met Glu Leu Ser Gly Leu Arg Tyr Asp Asp Thr Ala Ile Tyr Tyr Cys
                85                  90                  95

Val Arg Trp Ala Trp Asn Phe Asp Phe Leu Gly Trp Phe Asp Pro
                    100                 105                 110

Trp Gly Gln Gly Thr Leu Val Thr Val Ala Ser Ala Ser Thr Lys Gly
                115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430
```

Val Met His Glu Ala Leu His Asn His Tyr Thr Gln Lys Ser Leu Ser
            435                 440                 445

Leu Ser Pro Gly Lys
    450

<210> SEQ ID NO 91
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 92
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Ser Asp Thr Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser
        115                 120

<210> SEQ ID NO 93
<211> LENGTH: 219
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 93

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 94
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Ser Asp Thr Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Ala Asp Ala Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser
        115                 120

<210> SEQ ID NO 96
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Ala Asp Ala Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr

```
                     245                 250                 255
Leu Met Ile Ser Arg Thr Pro Glu Val Thr Cys Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 97
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Glu Ser Glu Thr Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser
        115                 120

<210> SEQ ID NO 98
<211> LENGTH: 453
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Glu |
| 1 | | | | 5 | | | | | 10 | | | | | 15 | |
| Ser | Leu | Lys | Ile | Ser | Cys | Lys | Val | Ser | Gly | Tyr | Ser | Phe | Thr | Ser | Gln |
| | | | 20 | | | | | 25 | | | | | 30 | | |
| Trp | Ile | Gly | Trp | Val | Arg | Gln | Met | Pro | Gly | Lys | Gly | Leu | Glu | Trp | Ile |
| | | 35 | | | | | 40 | | | | | 45 | | | |
| Gly | Met | Met | Tyr | Pro | Gly | Glu | Ser | Glu | Thr | Ile | Tyr | Ser | Pro | Ser | Phe |
| 50 | | | | | 55 | | | | | 60 | | | | | |
| Gln | Gly | Gln | Val | Thr | Ile | Ser | Ala | Asp | Asn | Ser | Ile | Ser | Thr | Ala | Tyr |
| 65 | | | | | 70 | | | | | 75 | | | | | 80 |
| Leu | Gln | Trp | Ser | Ser | Leu | Lys | Ala | Ser | Asp | Thr | Ala | Ile | Tyr | Tyr | Cys |
| | | | | 85 | | | | | 90 | | | | | 95 | |
| Ala | Ser | Gly | Pro | Gly | Tyr | Ser | Gly | Tyr | His | Tyr | Gly | Trp | Phe | Asp | Thr |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| | | 130 | | | | | 135 | | | | | 140 | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | | | 195 | | | | | 200 | | | | | 205 | |
| Asn | His | Lys | Pro | Ser | Asn | Thr | Lys | Val | Asp | Lys | Lys | Val | Glu | Pro | Lys |
| | | 210 | | | | | 215 | | | | | 220 | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | | | 275 | | | | | 280 | | | | | 285 | |
| Glu | Val | His | Asn | Ala | Lys | Thr | Lys | Pro | Arg | Glu | Glu | Gln | Tyr | Asn | Ser |
| | | | 290 | | | | | 295 | | | | | 300 | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Ser | Arg | Glu | Glu | Met | Thr | Lys | Asn | Gln |
| | | | | 355 | | | | | 360 | | | | | 365 | |
| Val | Ser | Leu | Thr | Cys | Leu | Val | Lys | Gly | Phe | Tyr | Pro | Ser | Asp | Ile | Ala |
| | | 370 | | | | | 375 | | | | | 380 | | | |

```
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 99
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Ala Asp Thr Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser
        115                 120

<210> SEQ ID NO 100
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Ala Asp Thr Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95
```

Ala Ser Gly Pro Gly Tyr Ser Gly Tyr His Tyr Gly Trp Phe Asp Thr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 101
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Ser Ser Asp Thr Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser
        115                 120

<210> SEQ ID NO 102
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Ser Ser Asp Thr Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 103
<211> LENGTH: 123
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 103

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Ser Asp Ala Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser
        115                 120

<210> SEQ ID NO 104
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Ser Asp Ala Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln

```
                355                 360                 365
Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 105
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Thr Asp Thr Ile Tyr Ser Pro Ser Phe
    50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser
        115                 120

<210> SEQ ID NO 106
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Asp Thr Asp Thr Ile Tyr Ser Pro Ser Phe
    50                  55                  60

Gln Gly Gln Val Thr Ile Ser Ala Asp Asn Ser Ile Ser Thr Ala Tyr
```

```
        65                  70                  75                  80
Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 107
<211> LENGTH: 123
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 107

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Glu Ser Asp Thr Ile Tyr Ser Pro Ser Phe
50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser
        115                 120

<210> SEQ ID NO 108
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Ser Gln
            20                  25                  30

Trp Ile Gly Trp Val Arg Gln Met Pro Gly Lys Gly Leu Glu Trp Ile
        35                  40                  45

Gly Met Met Tyr Pro Gly Glu Ser Asp Thr Ile Tyr Ser Pro Ser Phe
50                  55                  60

Gln Gly Gln Val Thr Ile Ser Ala Asp Asn Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Ser Gly Pro Gly Tyr Ser Gly Tyr His Tyr Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
            450
```